United States Patent
Nagasaki et al.

(10) Patent No.: US 12,049,543 B2
(45) Date of Patent: *Jul. 30, 2024

(54) COPOLYMER CONTAINING CYCLIC NITROXIDE RADICAL AND TRIALKOXYSILYL IN SIDE CHAIN, AND USE THEREOF

(71) Applicant: CrestecBio Inc., Ibaraki (JP)

(72) Inventors: Yukio Nagasaki, Ibaraki (JP); Takuya Inagaki, Ibaraki (JP); Binh Long Vong, Ibaraki (JP)

(73) Assignee: CrestecBio Inc., Ibaraki (JP)

( * ) Notice: Subject to any disclaimer, the term of this patent is extended or adjusted under 35 U.S.C. 154(b) by 200 days.

This patent is subject to a terminal disclaimer.

(21) Appl. No.: 16/477,604

(22) PCT Filed: Jan. 18, 2018

(86) PCT No.: PCT/JP2018/001438
§ 371 (c)(1),
(2) Date: Jul. 12, 2019

(87) PCT Pub. No.: WO2018/135592
PCT Pub. Date: Jul. 26, 2018

(65) Prior Publication Data
US 2019/0345293 A1    Nov. 14, 2019

(30) Foreign Application Priority Data
Jan. 19, 2017    (JP) .................................. 2017-007964

(51) Int. Cl.
| | |
|---|---|
| *C08G 81/02* | (2006.01) |
| *A61K 9/107* | (2006.01) |
| *A61K 9/51* | (2006.01) |
| *A61K 31/44* | (2006.01) |
| *A61K 31/4709* | (2006.01) |
| *A61K 31/785* | (2006.01) |
| *A61K 47/34* | (2017.01) |

(52) U.S. Cl.
CPC .......... *C08G 81/025* (2013.01); *A61K 9/1075* (2013.01); *A61K 9/5115* (2013.01); *A61K 31/44* (2013.01); *A61K 31/4709* (2013.01); *A61K 31/785* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 3,884,886 | A  * | 5/1975 | Plueddemann | ............ C08J 5/08 |
| | | | | 526/258 |
| 8,980,241 | B2 * | 3/2015 | Nagasaki | ................ A61P 39/06 |
| | | | | 424/78.17 |
| 9,333,265 | B2 * | 5/2016 | Nagasaki | ................ A61P 13/12 |
| 2011/0142787 | A1 | 6/2011 | Nagasaki et al. | |
| 2014/0356315 | A1 | 12/2014 | Nagasaki et al. | |
| 2015/0118310 | A1 | 4/2015 | Nagasaki et al. | |
| 2017/0247491 | A1 | 8/2017 | Nagasaki | |

FOREIGN PATENT DOCUMENTS

| | | |
|---|---|---|
| JP | 2010-243563 | 10/2010 |
| JP | 2011-173960 | 9/2011 |
| WO | 2009/133647 | 11/2009 |
| WO | 2013/111801 | 8/2013 |
| WO | 2013/118783 | 8/2013 |
| WO | 2016/052463 | 4/2016 |

OTHER PUBLICATIONS

Nagasaki et al. (Biomaterials Science, 2014, 2, 522-529.*
Yoshitomi et al. (Biomater. Sci., 2015, 3, 810-815).*
Nagasaki et al. Biomaterials Science, 2014, 2, 522-529. (Year: 2014).*
Yoshitomi et al. Biomaterials Science, 2015, 3, 810-815. (Year: 2015).*
Yoshitomi et al. "Redox nanoparticle therapeutics to cancer—increase in therapeutic effect . . . " Journal of Controlled Release, 2013, 172(1), 137-143.*
Cleanlink (https://www.cleanlink.com/cp/article/Alcohol-vs-Non-alcohol-based-Hand-Sanitizers--15230, year: 2013, no pagination).*
Long, G. et al. "N, N-Dimethylformamide" Concise Internat. Chem. Assessment Document 31, p. 1-55, 2001, https://apps.who.int/iris/bitstream/handle/10665/42368/9241530316.pdf?sequence=1 (Year: 2001).*
International Search Report dated Apr. 10, 2018 in International (PCT) Application No. PCT/JP2018/001438.
Hossain et al., "Silica-installed redox nanoparticles for novel oral nanotherapeutics-improvement in intestinal delivery with anti-inflammatory effects", Journal of Drug Targeting, vol. 22, No. 7, 2014, pp. 638-647.

* cited by examiner

*Primary Examiner* — Erin E Hirt
(74) *Attorney, Agent, or Firm* — Wenderoth, Lind & Ponack, L.L.P.

(57) ABSTRACT

A copolymer which includes hydrophilic and hydrophobic blocks, which can form nanoparticles in which a physiologically active substance can be efficiently packaged therein and which are stable under acidic conditions. The hydrophilic segment of the copolymer is composed of polyethylene glycol (PEG) and the hydrophobic segment is composed of polystyrene. The hydrophobic segment has a side chain, and the side chain has ends to which a cyclic nitroxide radical having a radical scavenging function and a trialkoxysilane are covalently bonded.

10 Claims, 17 Drawing Sheets

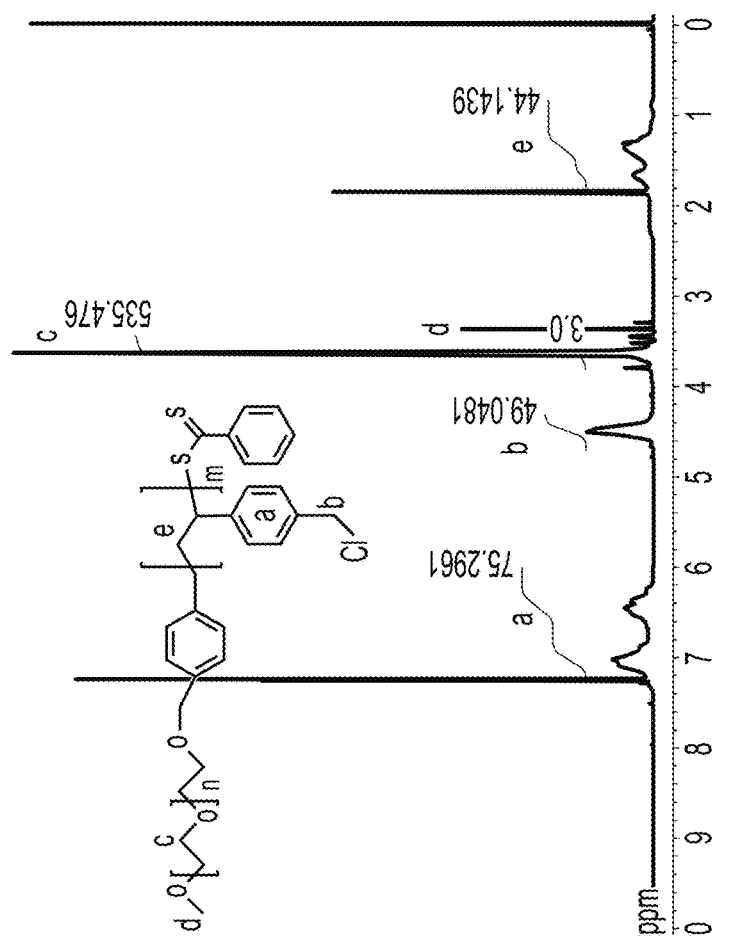
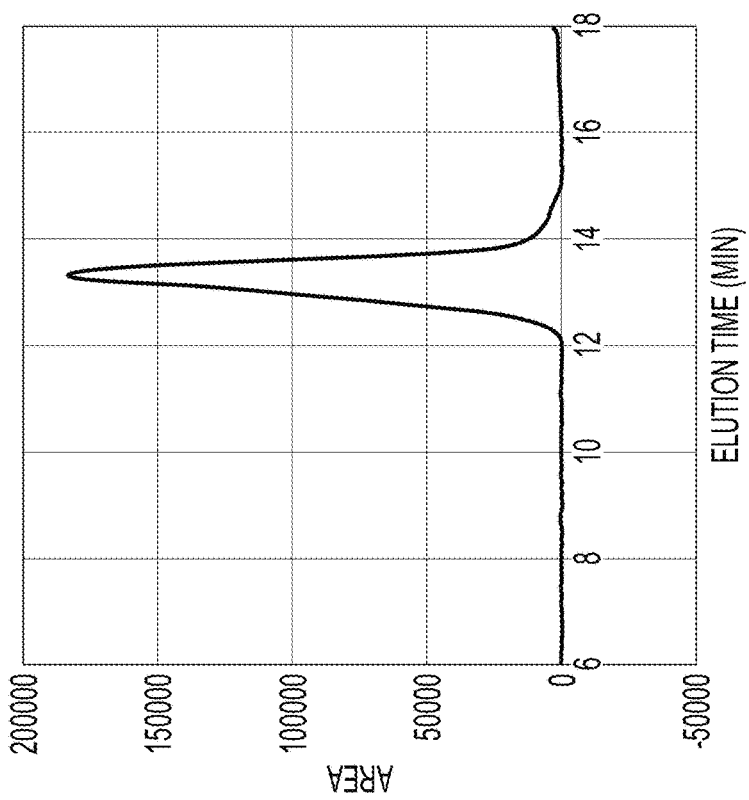
[Fig. 1]

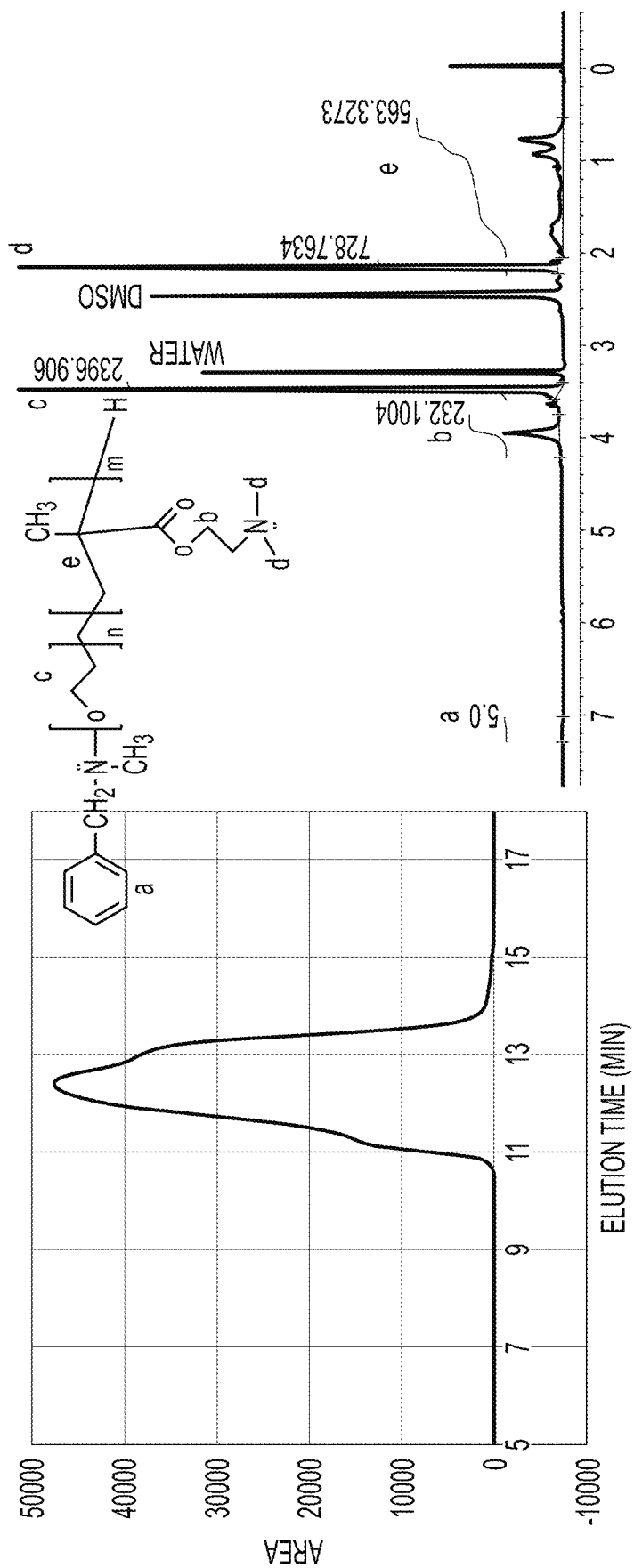
[Fig. 2]

[Fig. 3]
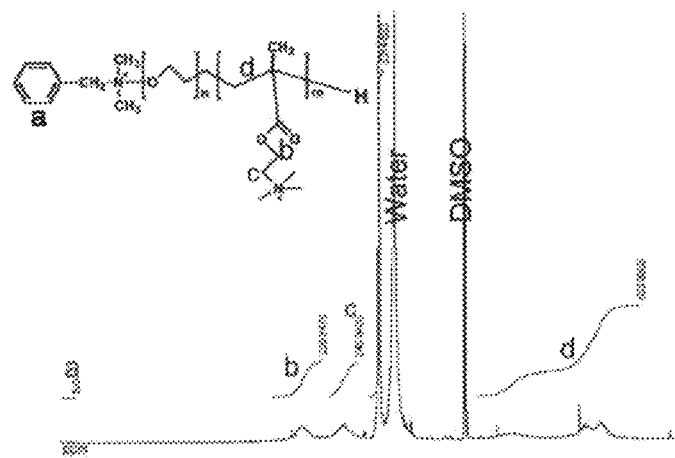

[Fig. 4]
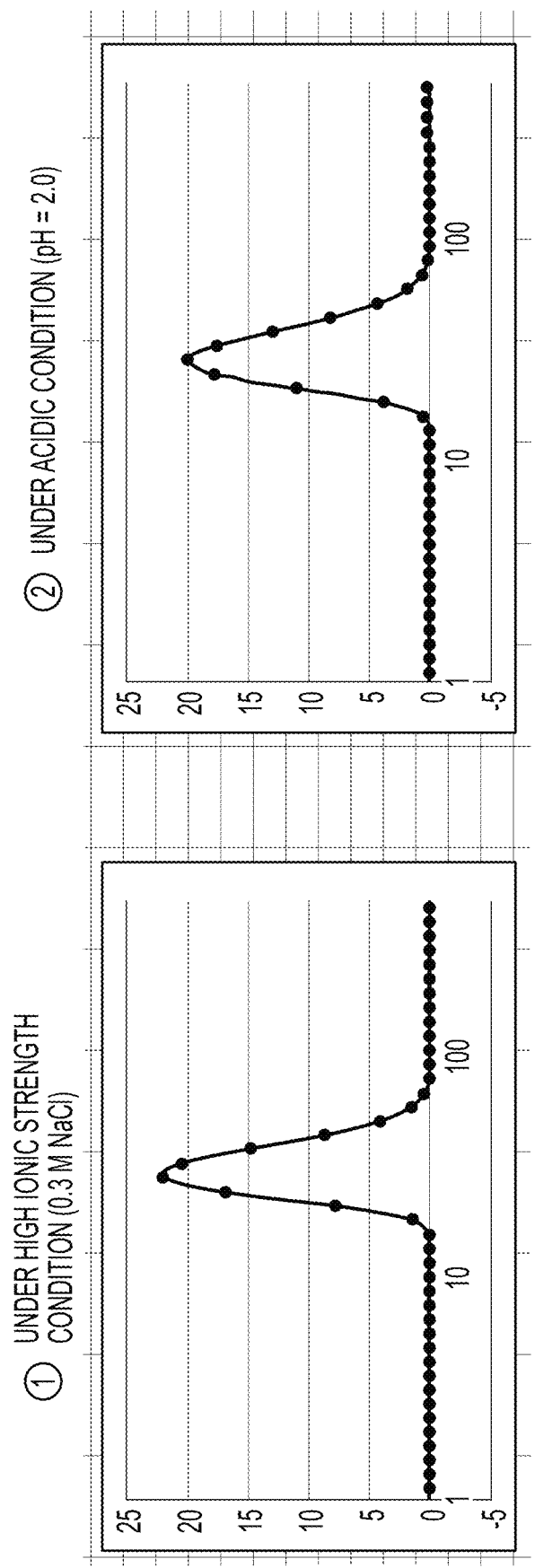

[Fig. 5]
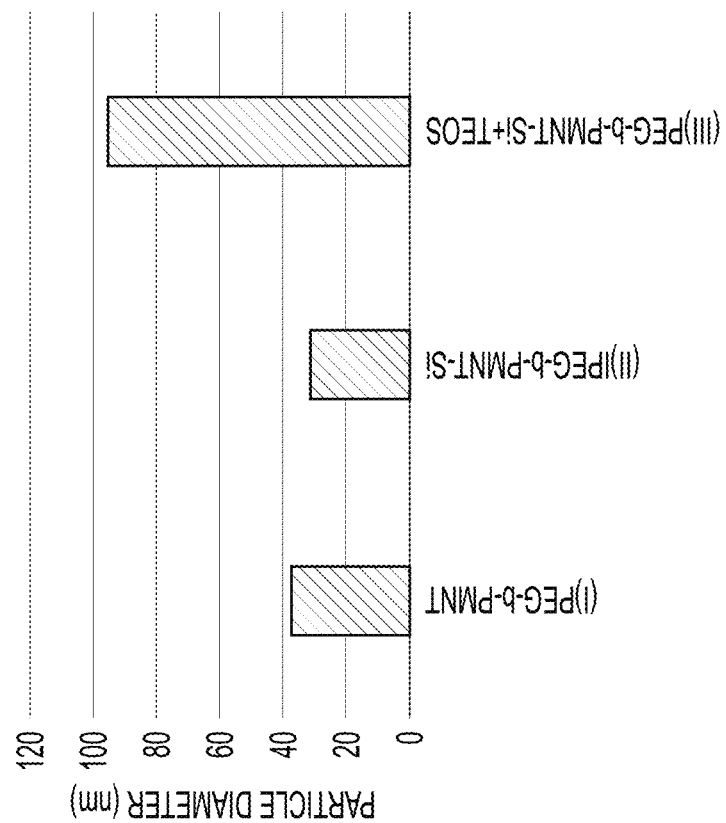
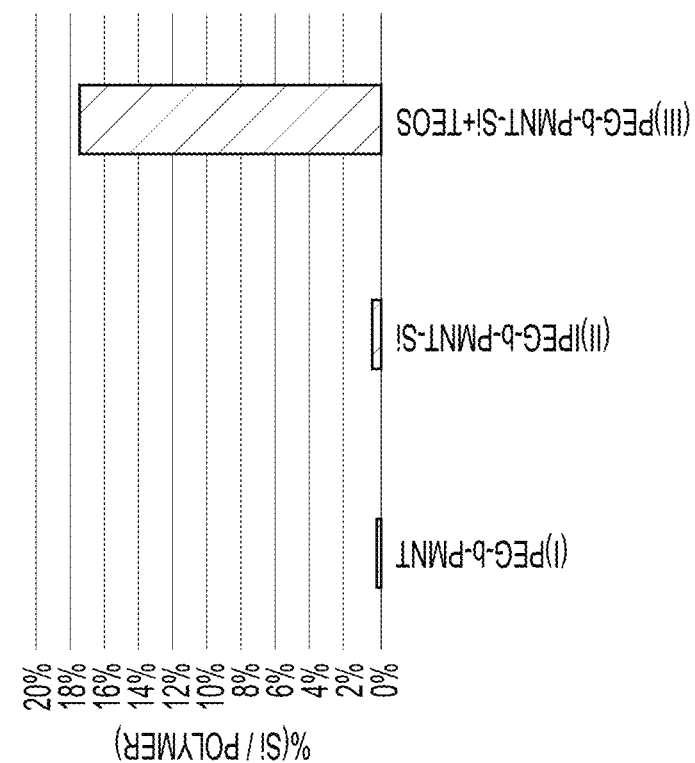

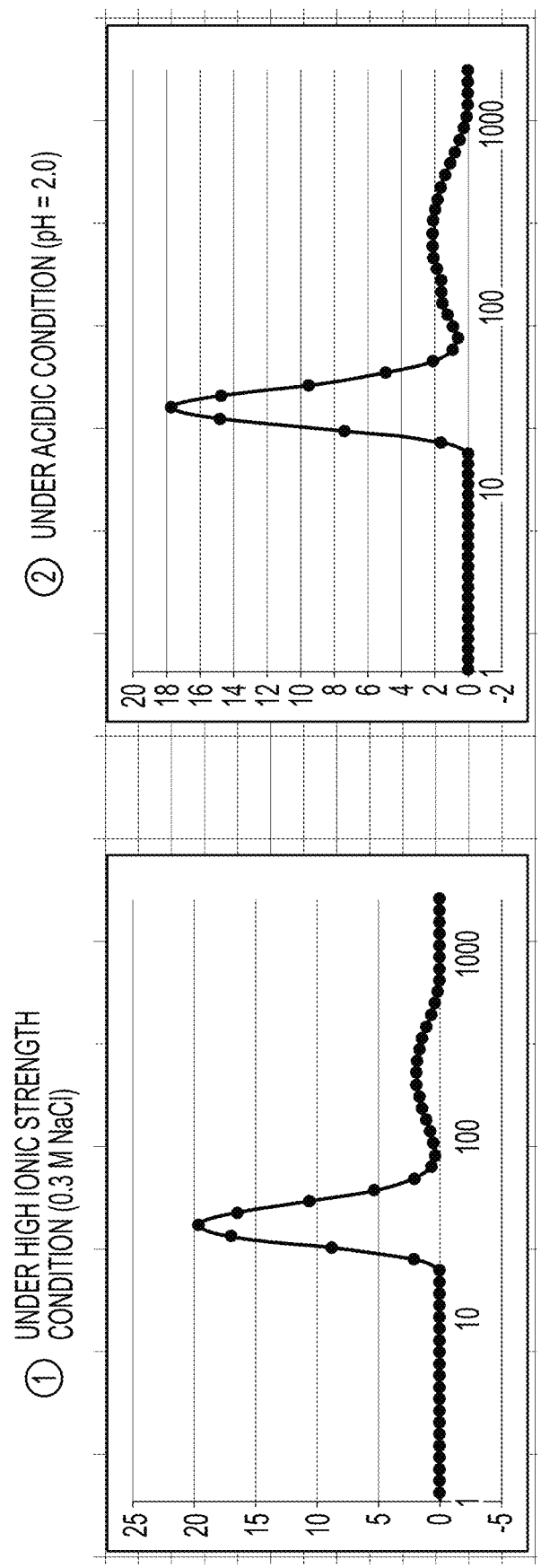
[Fig. 6]

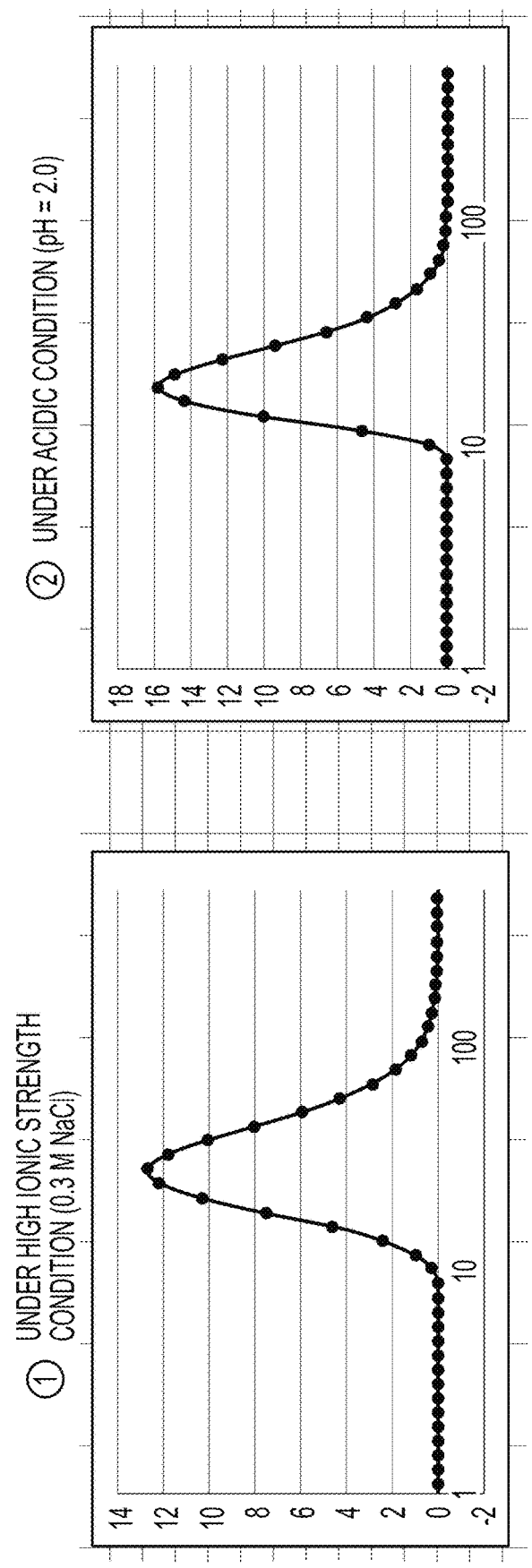

[Fig. 8]
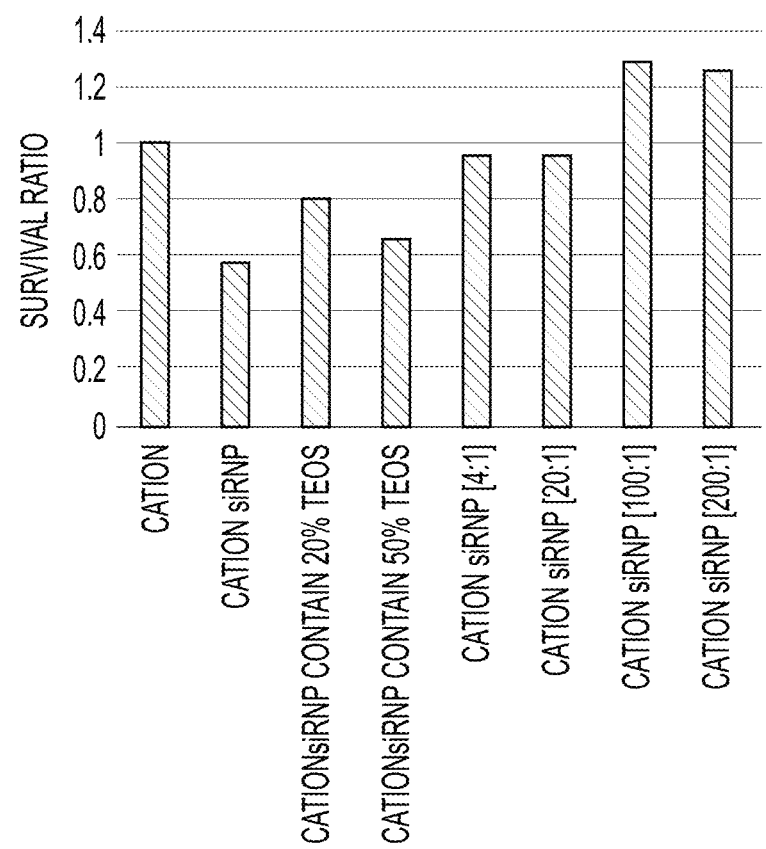

[Fig. 9]
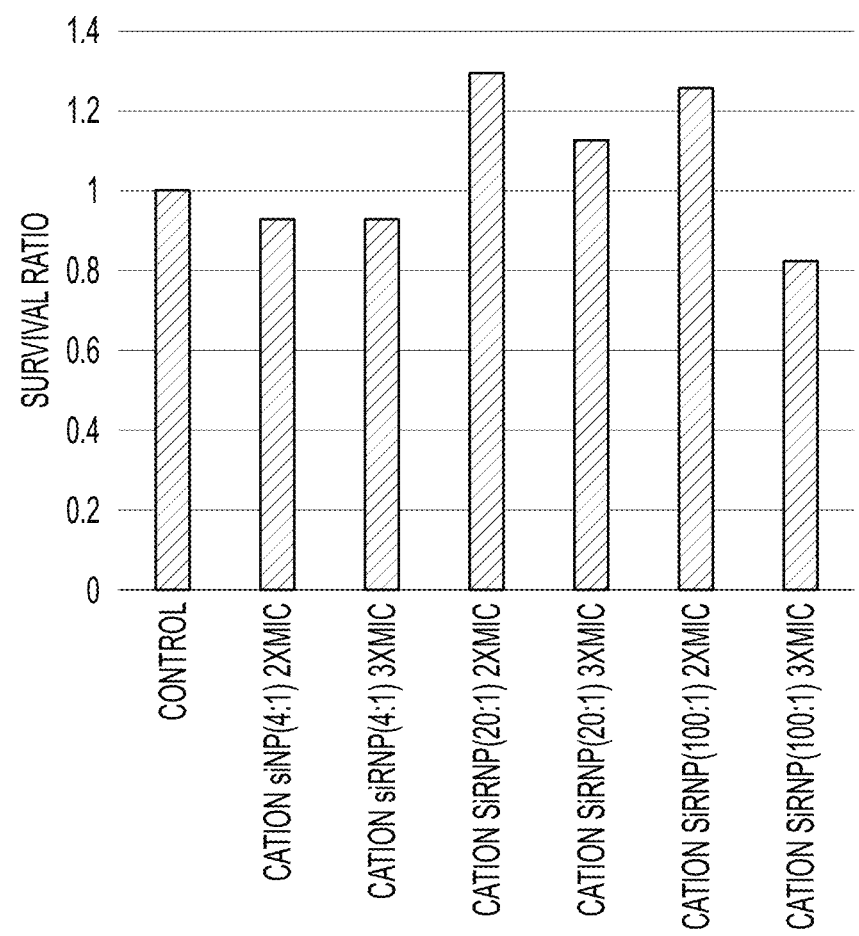

[Fig. 10]
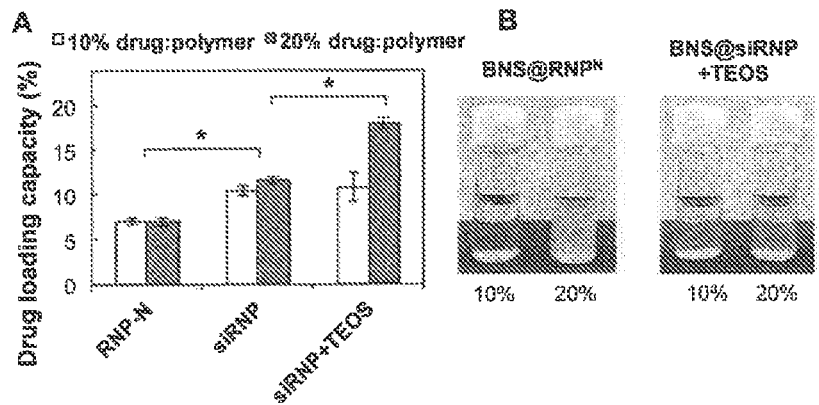
[Fig. 11]
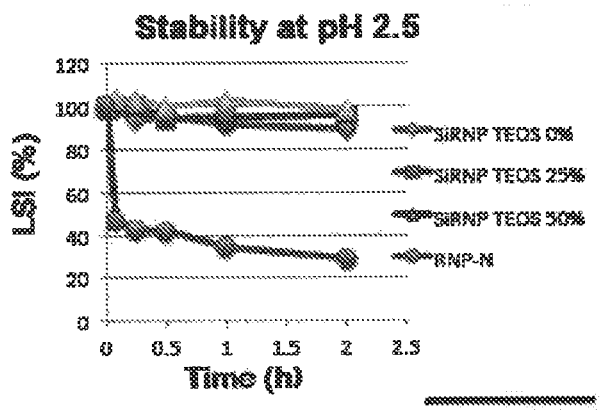
[Fig. 12]
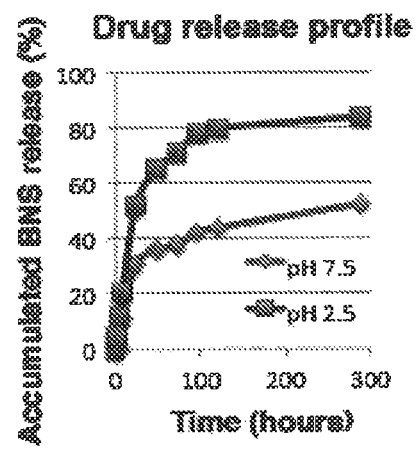

[Fig. 13]
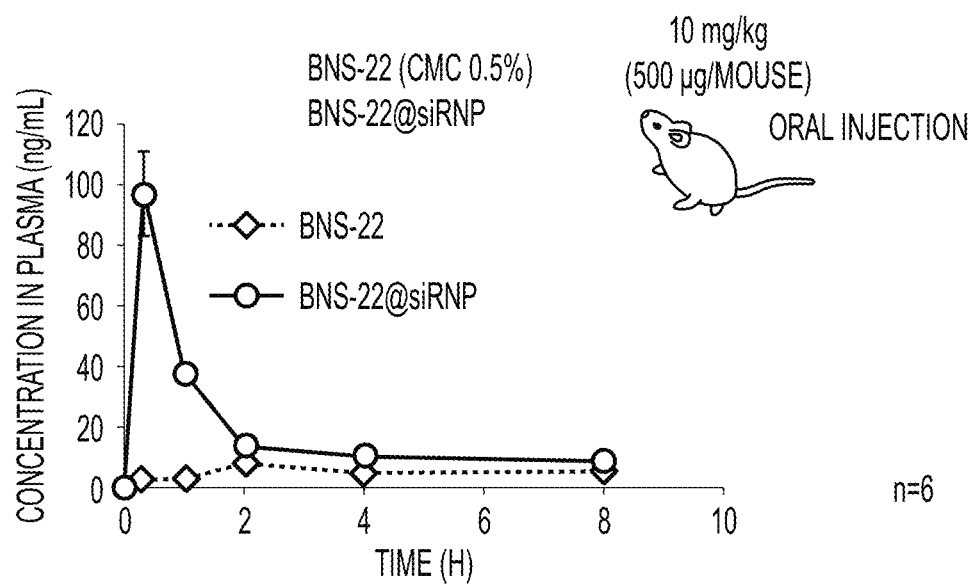

[Fig. 14]
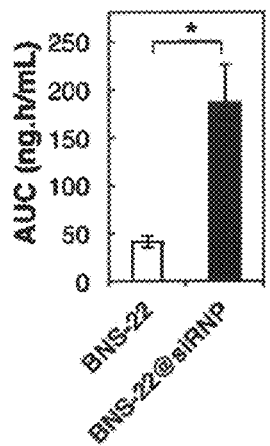
[Fig. 15]
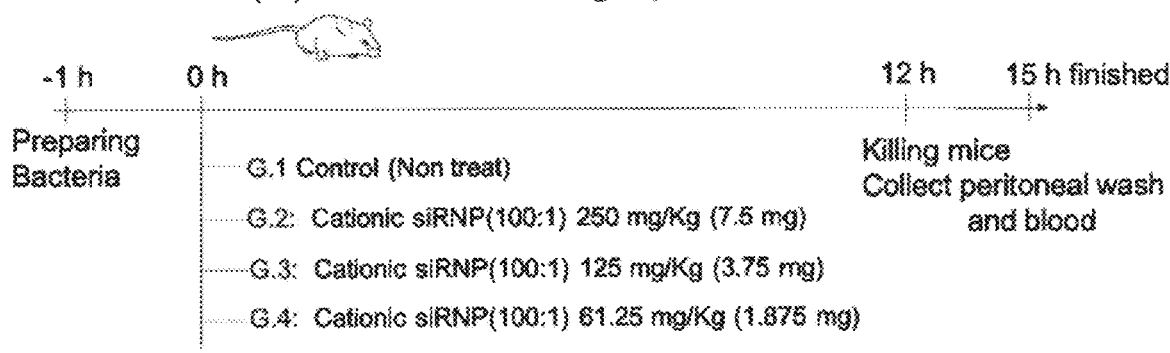

[Fig. 16]
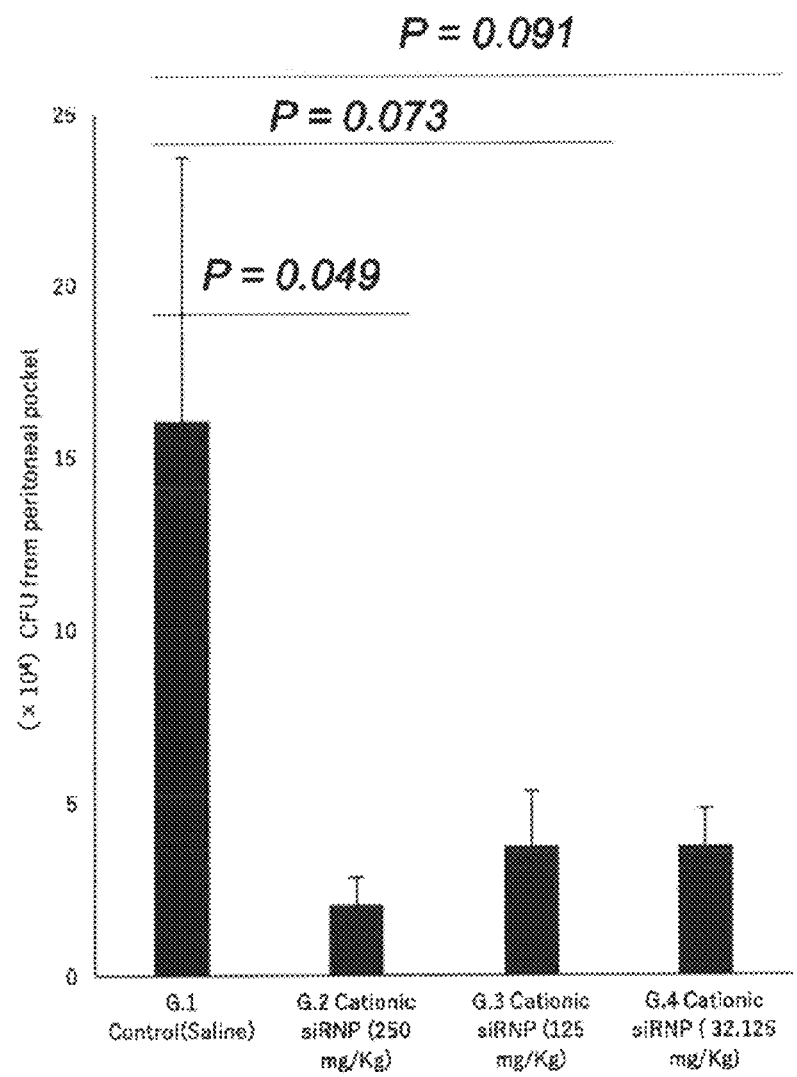

[Fig. 17]
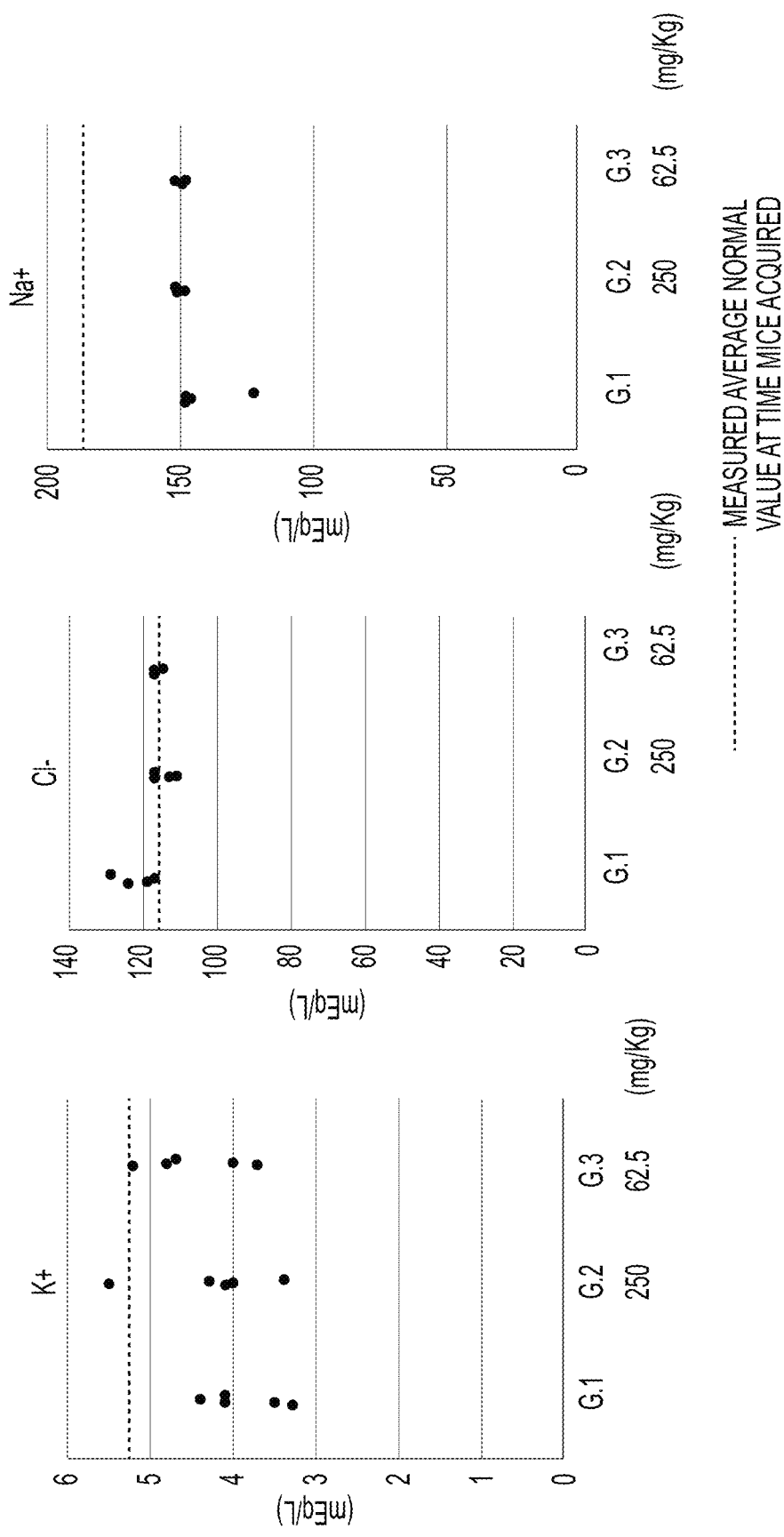

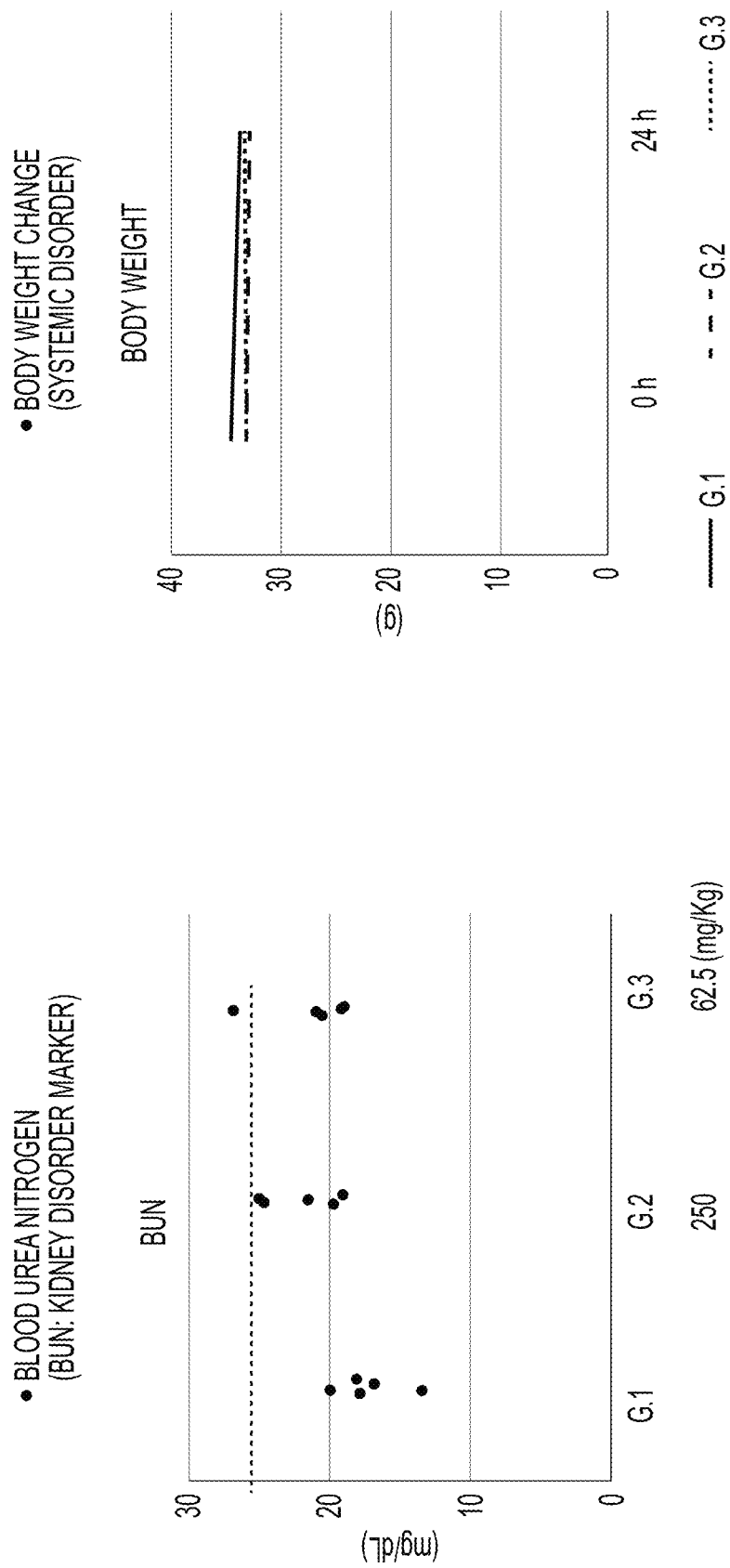
[Fig. 18]

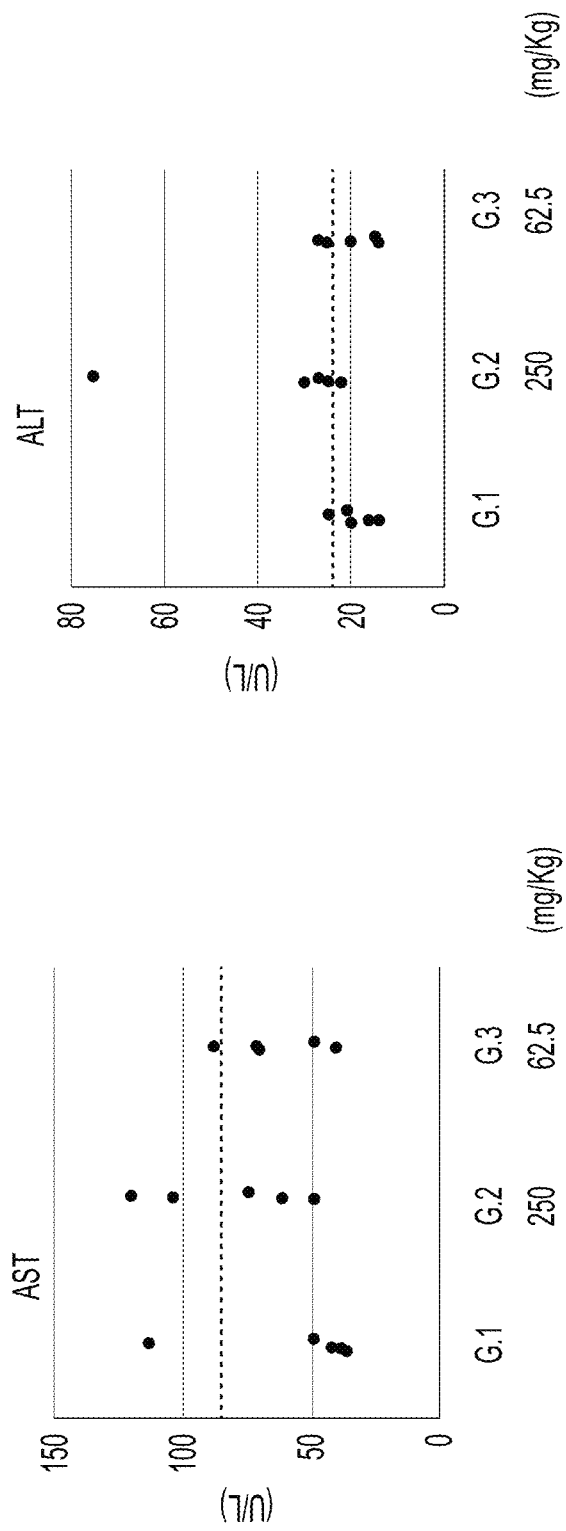
[Fig. 19]

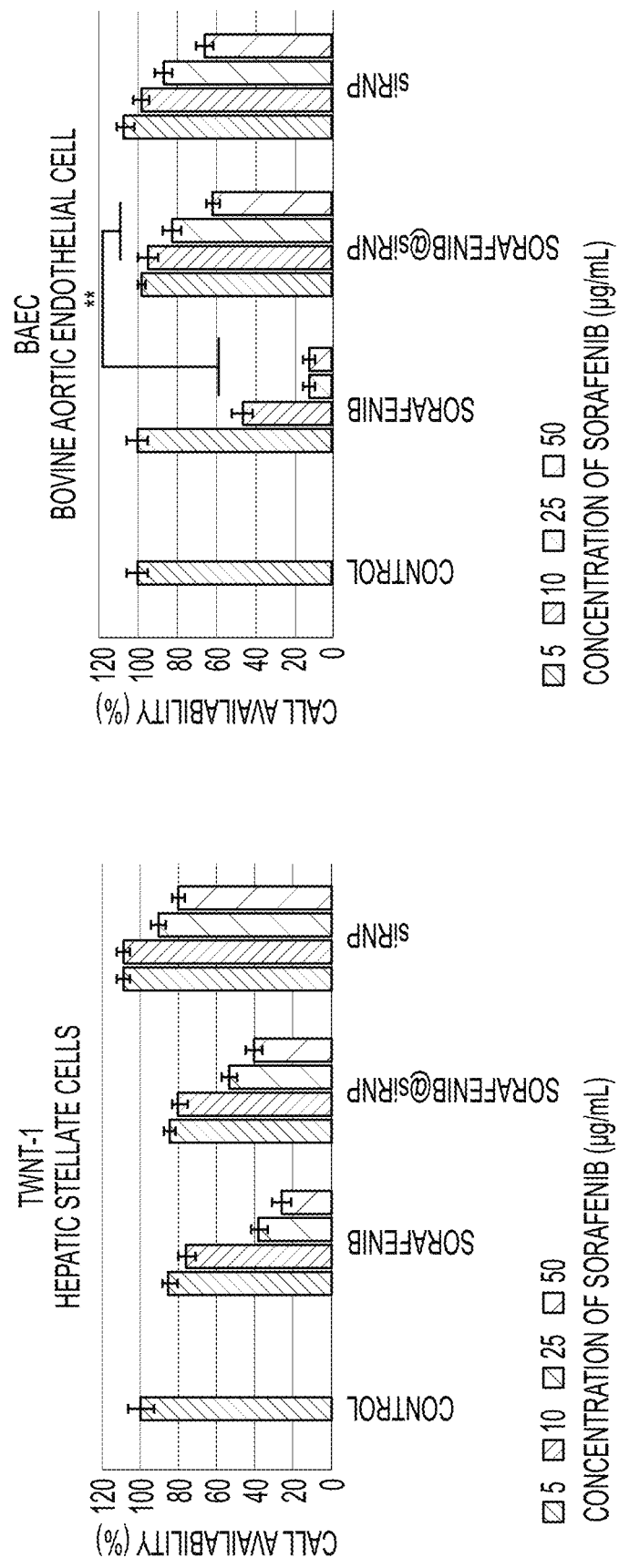
[Fig. 20]

COPOLYMER CONTAINING CYCLIC NITROXIDE RADICAL AND TRIALKOXYSILYL IN SIDE CHAIN, AND USE THEREOF

TECHNICAL FIELD

The present invention relates to a copolymer in which a hydrophilic segment is composed of polyethylene glycol (PEG) and a hydrophobic segment is composed of polystyrene, the hydrophobic segment having a side chain and the side chain having ends to which a cyclic nitroxide radical having a radical scavenging function and a trialkoxysilane are covalently bonded, and to the use of the copolymer as a carrier of a physiologically active substance.

BACKGROUND ART

Copolymers in which a hydrophilic segment is composed of polyethylene glycol (PEG) and a hydrophobic segment is composed of polystyrene and contain a cyclic nitroxide radical having a radical scavenging function in a side chain of the hydrophobic segment have been confirmed to be able to prevent or treat various types of disorders considered to be caused by the excess production or presence of active oxygen in the living body by using a redox mechanism capable of being demonstrated by nitroxide radicals after having acquired stability in the body's environment as a result of the cyclic nitroxide radical having been polymerized (for example see Patent Document 1). Compared to organic nanoparticles prepared by automatically assembling in a system containing such a copolymer but not containing silica, nanoparticles of an organic-inorganic hybrid complex containing such a copolymer and silica have improved stability under acidic conditions, for example, and these nanoparticles have been confirmed to be able to be used as carriers of certain drugs (for example see Patent Document 2, Non-Patent Document 1).

However, there are cases in which drugs cannot necessarily be packaged (or encapsulated) efficiently in nanoparticles of this complex, and there is room for improvement particularly when targeting drugs having the potential for activity to be detrimentally affected by degeneration and the like of the drug under the treatment conditions.

PRIOR ART DOCUMENT

Patent Document

Patent Document 1: WO 2009/133647
Patent Document 2: WO 2013/118783

Non-Patent Document

Non-Patent Document 1: Hossain, A., et al., J. Drug. Target, 2014; 22(7): 638-647

SUMMARY OF INVENTION

Technical Problem

There is a demand to provide a copolymer that is able to solve the above-mentioned problems, and in particular, is able to efficiently encapsulate a drug (or physiologically active substance) under conditions for which there is less potential for having a detrimental effect on the activity of the drug, as well as demonstrate the function of a cyclic nitroxide radical contained in a side chain of a hydrophobic segment.

Solution to Problem

The inventors of the present invention have found that, in a copolymer in which a hydrophilic segment is composed of polyethylene glycol (PEG) and a hydrophobic segment is composed of polystyrene, and contains a cyclic nitroxide radical having a redox or radical scavenging function in a side chain of the hydrophobic segment, when a trialkoxysilyl group is introduced into the side chain of the hydrophobic segment in addition to the cyclic nitroxide radical by covalent bonding, not only stable nanoparticles are formed in various types of solutions due to crosslinking of the copolymer per se, but when this copolymer is treated along with tetraalkoxysilane or nanosized silica with a certain drug also present in these systems, silica-containing redox nanoparticles can be provided that have a physiologically active substance or drug efficiently encapsulated therein at a high content rate at a temperature equal to or lower than the ambient temperature, for example a temperature within a range from 10° C. to 30° C.

Thus, inventions of the following aspects are provided by the present invention.

(1) A copolymer represented by the following formula (I):

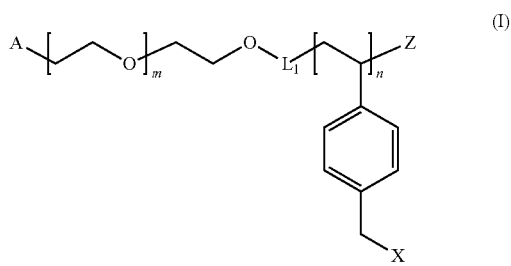

wherein,

A represents a non-substituted or substituted $C_1$-$C_{12}$ alkoxy group, the substituent in the case of being substituted represents a formyl group or R'R"CH— group, where R' and R" independently represent $C_1$-$C_4$ alkoxy or R' and R" may combine together to form —OCH$_2$CH$_2$O—, —O(CH$_2$)$_3$O— or —O(CH$_2$)$_4$O—;

$L_1$ may be selected from groups represented by the formula

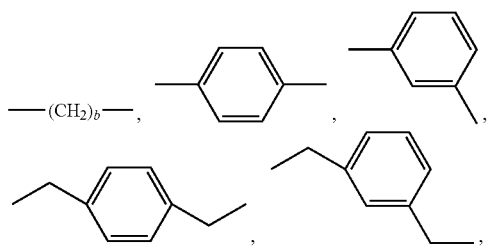

or may be selected from the group consisting of a single bond, —(CH$_2$)$_b$S—, —CO(CH$_2$)$_b$S—, —(CH$_2$)$_b$NH—, —(CH$_2$)$_b$CO—, —CO—, —OCOO—, and —CONH—;

X individually contains a group described in the following (a), (b) and (c):

(a) group represented by $L_2$-$R_1$, wherein $L_2$ represents —$(CH_2)_a$—NH—$(CH_2)_a$— or —$(CH_2)_a$—O—$(CH)_a$— and $R_1$ is represented by any of the following formulas:

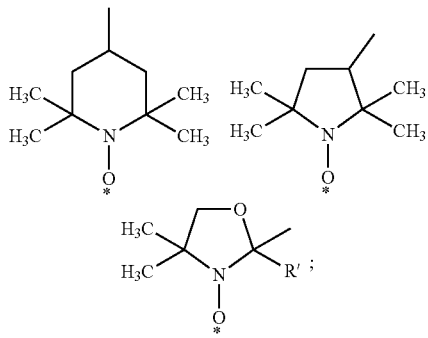

(b) group represented by $L_3$-$R_2$, wherein $L_3$ is the same as defined for $L_2$, $R_2$ is represented by the formula: —$(CH_2)_k$—Si(O-Alk)$_3$, and each Alk is a $C_{1-4}$ alkyl that may be the same as or different from another Alk;

(c) group represented by $R_3$, wherein $R_3$ is chloro, bromo, or hydroxy, and units present in a polymer main chain having (a), (b) and (c) are randomly present, units having (a) are within the range of 2 to 99, units having (b) are within the range of 1 to 98, and units having (c) are either not present or within the range of 1 to 20, provided that the total number of these units is n;

Z is H, SH, or S(C=S)-Ph, wherein Ph represents phenyl optionally substituted with one or two groups of methyl or methoxy;

each a independently represents 0 or an integer of 1 to 5;

b represents an integer of 1 to 5;

k represents an integer of 1 to 18;

m represents an integer of 2 to 10,000; and n represents an integer of 3 to 100.

(2) The copolymer described in (1) above, wherein $L_1$ represents paraxylylene, metaxylylene or —$CH_2CH_2S$—, $L_2$ represents —NH— or —O—, and each of the Alk is the same as another.

(3) A pharmaceutical composition including the copolymer represented by formula (I) of (1) and a poly(quaternary amine) antibacterially active substance.

(4) The composition of (3), wherein the antibacterially active substance is a compound represented by the formula:

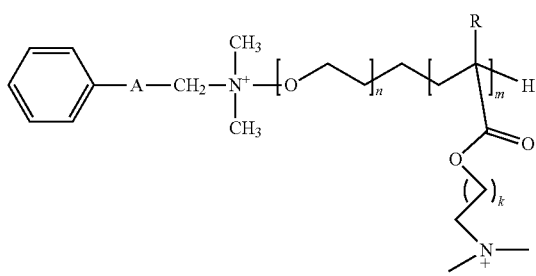

wherein,

A is represented by —$(CH_2)_j$—, where j represents 0 or an integer of 1 to 17;

R represents a hydrogen atom or methyl group; and at least one of 1 to 5 hydrogen atoms in phenyl may be replaced with $C_{1-6}$ alkyl, $C_{1-6}$ alkoxy, or hydroxy.

(5) A pharmaceutical composition including the copolymer represented by formula (I) of (1) and a hydrophobic anticancer drug.

(6) The composition of (5), wherein the hydrophobic anticancer drug is selected from the group consisting of BNS-22 (8-[(3,4-dihydro-2H-quinolin-1-yl)carbonyl]-5,7-dimethoxy-4-propyl-2H-chromen-2-one), sorafenib, camptothecin, paclitaxel, and anticancer platinum complex.

(7) The composition of any one of (3) to (6), which forms nanosized micellar particles in an aqueous medium.

(8) Silica-containing redox nanoparticles for medical use including a biologically active substance encapsulated or filled therein, wherein the silica-containing nanoparticles are immobilized on nanosized silica particles via a copolymer of -$L_3$-$(CH_2)_k$—Si(O-Alk)$_3$ represented by formula (I) defined in (1), and have a structure in which a physiologically active substance is bound to or adsorbed on the silica particles.

(9) The silica-containing redox nanoparticles described in (8) above, wherein the physiologically active substance is an antibacterial compound represented by the formula:

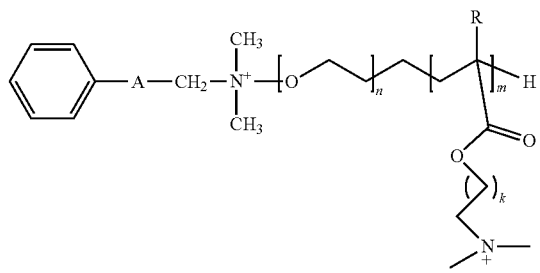

wherein,

A is represented by —$(CH_2)_j$—, where j is an integer of 0 or 1 to 17;

R represents a hydrogen atom or methyl group; and at least one of 1 to 5 hydrogen atoms in phenyl may be replaced with $C_{1-6}$ alkyl, $C_{1-6}$ alkoxy, or hydroxy; or an anticancer drug selected from the group consisting of BNS-22, sorafenib, camptothecin, paclitaxel, and anticancer platinum complex.

(10) A method of producing silica-containing redox nanoparticles including a physiologically active substance filled therein, the method including a step of dialyzing, against water at a temperature equal to or lower than the ambient temperature, the copolymer described in (1) alone, or a combination of the copolymer with:

(i) tetraalkoxysilane represented by Si(O-Alk)$_4$, wherein each Alk is a $C_{1-4}$ alkyl group that may be the same as or different from another Alk; or (ii) a physiologically active substance in the form of a poly(quaternary amine) antibacterial compound or hydrophobic anticancer drug in a water-soluble solution in a dialysis container containing nanosized silica particles.

Effects of Invention

According to the present invention, a copolymer represented by formula (I) is provided, and this copolymer not only forms stable nanoparticles in various types of solutions due to crosslinking of the copolymer per se, but is capable of providing silica-containing redox nanoparticles efficiently packaged with a physiologically active substance by treating the copolymer, the copolymer and a tetraalkoxysilane or nanosized silica, or a certain physiologically active substance also present in these systems.

BRIEF DESCRIPTION OF DRAWINGS

FIG. 1 indicates the separation spectrum and the $^1$H-NMR spectrum of PEG-b-PCMS produced in Production Example 1 as determined using a size exclusion chromatography (SEC) column.

FIG. 2 indicates the $^1$H-NMR spectrum of BMA-PEG-b-PDMAEMA produced in Production Example 3.

FIG. 3 indicates the $^1$H-NMR spectrum of BDMA-PEG-b-PTMAEMA produced in Production Example 4.

FIG. 4 indicates the light scattering spectrum of silica-containing redox nanoparticles (siRNP) using TEOS produced in Production Example 5 (left: under a condition of high ionic strength, right: under a condition of pH=2).

FIG. 5 indicates the results for silica-containing redox nanoparticles (siRNP) using TEOS produced in Production Example 5, with the graph on the left side indicating the Si content per polymer of each particle and the graph on the right side indicating the particle diameter of each particle.

FIG. 6 indicates the light scattering spectrum under high ionic strength (left) and the light scattering spectrum under acidic conditions (right) of the siRNP obtained in Production Example 6.

FIG. 7 indicates the light scattering spectrum under high ionic strength (left) and the light scattering spectrum under acidic conditions (right) of the siRNP obtained in Production Example 7.

FIG. 8 indicates the results of evaluating toxicity using BAEC in Test 2.

FIG. 9 indicates the results of evaluating toxicity at higher concentration using BAEC in Test 2.

FIG. 10 indicates the drug encapsulation efficiency of silica-containing redox nanoparticles in Production Example 9(1).

FIG. 11 indicates the results of a stability test under acidic conditions of drug-encapsulating silica-containing redox nanoparticles in Production Example 9(2).

FIG. 12 indicates the results of an in vitro drug release test in Production Example 9(3).

FIG. 13 indicates the results of an in vivo drug release test in Production Example 9(4).

FIG. 14 indicates the results of AUC analyses in Production Example 9(4).

FIG. 15 summarizes the protocol of a test for evaluating the antibacterial ability of Cation siRNP in mouse abdominal cavity in Test 3.

FIG. 16 indicates the results of a test for evaluating antibacterial ability in Test 3.

FIGS. 17 to 19 indicate the results of toxicity evaluation tests during administration of Cation siRNP into the abdominal cavity of mice in Test 4.

FIG. 20 indicates the results of a test for evaluating the efficacy of sorafenib siRNP prepared in Production Example 10 against fibrosis.

DESCRIPTION OF EMBODIMENTS (A) Copolymer

The copolymer represented by formula (I) can be alternatively represented by the formula below.

(I-a)

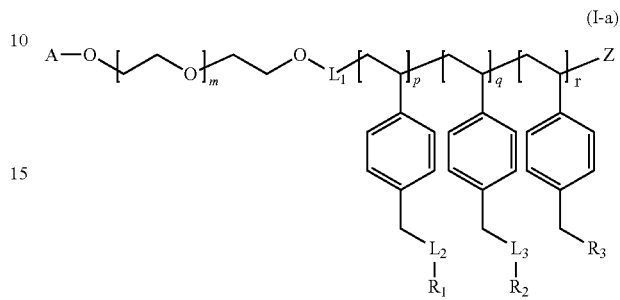

In the formula, A, $L_1$, Z, m, $L_2$-$R_1$, $L_3$-$R_2$ and $R_3$ are the same as previously defined for the above-mentioned formula (I), p represents an integer of 2 to 99, q represents an integer of 1 to 99, r represents 0 or an integer of 1 to 20 provided that p+q+r is 3 to 100(n), and although the repeating units indicated with p, q, and r are randomly present, they may combine together to form a different block segment from the block segment of the repeating unit indicated with m.

This polymer forms nanosized (approx. 25 nm to approx. 45 nm on average) particles that do not easily collapse under high ionic strength conditions (such as an aqueous solution of 0.3 M) and acidic conditions (pH=2.0) in an aqueous solution or homogeneous dispersion.

With respect to the present invention, nanosized particles or nanoparticles refer to particles for which the average diameter thereof is within the nanometer size range in the case of having analyzed by dynamic light scattering (DLS) in an aqueous solution or homogeneous dispersion containing those particles.

In the case it is desirable that the surface of the particles does not exhibit chemical reactivity, A is preferably non-substituted $C_{1-12}$ alkyl, more preferably $C_{1-6}$ alkoxy, and most preferably $C_1$ alkoxy(methyl).

Without being limited by the definition of A and throughout the entire present invention, in the case of indicating in the manner of a $C_{a-z}$ alkoxy group or alkyl group, this refers to a linear or branched alkoxy group or alkyl group having a to z number of carbon atoms, and examples of an alkyl moiety or alkyl group include, but are not limited to, methyl, ethyl, n-propyl, iso-propyl, n-butyl, sec-butyl, pentyl, hexyl, heptyl, octyl, decyl, and undecyl.

$L_1$ is preferably a paraxylylene, metaxylylene, or a —(CH$_2$)$_a$S— linking group, $L_2$ is preferably —NH— or —O— for which a in the definition is 0 and more preferably —NH—. In the case of having different meanings depending on bond directionality like $L_1$ and $L_2$, it is intended to refer to those bonded in the directionality indicated, and for example, in the case of the linking group —(CH$_2$)$_2$S—, the S atom refers to bonding with the repeating unit indicated with n in formula (I).

The unit in the polymer main chain having a group described in (a), (b), and (c) in formula (I), the unit of the polymer main chain having a group described in (c) among those units indicated with p, q, and r in formula (I-a), or the unit indicated with r in formula (I-a) are not required to be present in order to achieve the object of the present invention.

In $L_3$-$R_2$, $L_3$ is the same as defined for $L_2$, preferably is —NH— or —O—, $R_2$ is —$(CH_2)_k$—Si(O-Alk)$_3$, and k is an integer of 2 to 12 and more preferably an integer of 3 to 8. In addition, m is preferably 12 to 1000 and more preferably 50 to 500, n is preferably 6 to 80 and more preferably 10 to 60, p is an integer is 3 to 80, q is an integer of 3 to 80, r is preferably not present, and p and q are preferably each 5 or more.

This copolymer can be present as nanosized micellar particles or nanoparticles having a hydrophobic segment for the core and a hydrophilic segment for the shell in water or an aqueous medium or aqueous solution having increased ionic strength or containing a buffer.

Although not limited thereto, the above-mentioned copolymer can be successfully provided by using for the raw material thereof a copolymer in which the hydrophilic segment thereof contains polyethylene glycol (PEG) and the hydrophobic segment thereof contains polystyrene, and a halomethylene, and particularly chloromethylene, is contained in a side chain of the hydrophobic segment (to also be referred to as PEG-b-PCMS, hereinafter), and by introducing a cyclic nitroxide radical and an -$L_3$-$R_2$ group, wherein $L_3$ is NH or O and $R_2$ is a $(CH_2)_k$—Si(O-Alk)$_3$ group, by covalently bonding through the halomethylene of PCMS. When introducing these groups into PCMS, it is recommended to use a compound having an amino group or hydroxy group for the moiety corresponding to $L_3$ as a reactant for introducing $L_3$. PEG-b-PCMS can generally be produced according to the method described in WO 2016/052463 or the above-mentioned Patent Document 1. A typical example of the method described in the former is explained in the production examples which will be described later.

(B) Use of Copolymer

Although the copolymer represented by formula (I) forms nanosized particles per se, when forming these particles, the silica content able to be present in the core can be controlled and increased by having in the co-presence of a tetraalkoxysilane of Si(O-Alk)$_4$ (wherein, each Alk is $C_{1-4}$ alkyl that may be the same as or different from another Alk but is preferably the same as another) or nanosized silica (silica sol), and particularly when using a tetraalkoxysilane, particles can be obtained in which the silica content increases corresponding to the a used mount thereof. In this manner, according to the present invention, nanosized silica-containing particles can be provided containing silica in the core region, having a hydrophobic portion present around the periphery thereof that is derived from the copolymer of formula (I), and has a PEG chain of the hydrophilic portion present in the shell moiety surrounding the core. These nanosized silica-containing particles are also useful with respect to being able to be used to adsorb and scavenge, for example, contaminating substances in the body by using the silica contained therein.

As described in Non-Patent Document 1, for example, although conventional silica-containing redox particles are required to be prepared at a comparatively high temperature (e.g. 80° C.) at which typical physiologically active substances are susceptible to detrimental effects, the copolymer of formula (I) is characterized in that, due to the presence of —$(CH_2)_k$—Si(O-Alk)$_3$ of the $L_3$-$R_2$ group linked via —NH— or —O—, target nanosized silica-containing redox particles can be prepared at a comparatively low temperature (temperature equal to or lower than the ambient temperature such as 10° C. to 30° C.), and is further characterized in that the silica content obtained using tetraalkoxysilane can be controlled. In addition, these characteristics are not lost even when forming particles by combining with various physiologically active substances (having completely different chemical properties in the manner of poly(quaternary amine) antibacterial agents or hydrophobic anticancer drugs) in systems allowing the formation of particles. Thus, according to the present invention, a pharmaceutical composition can also be provided comprising the copolymer of formula (I) (together with silica derived from nanosized silica (silica sol) as necessary), which can form the above nanoparticles, and a poly(quaternary amine) antibacterially active compound or hydrophobic anticancer drug. Although the optimum value of the mixing ratio between the copolymer of formula (I) and the silica derived from nanosized silica (silica sol) and physiologically active substance optionally contained therein in the composition can be varied depending on each component selected, there are no particular limitations thereon provided nanomicelles can be formed in an aqueous medium, and a preferable ratio can be determined by referring to the production examples and test examples will be described later.

Silica-containing redox nanoparticles of the aspect of (8) above can also be provided by freeze-drying or centrifugally separating, for example, the nanosized micellar particles formed from this composition in an aqueous medium.

Nanoparticles containing or not containing a physiologically active substance or drug are stable particles that do not aggregate under high ionic strength and do not collapse under acidic conditions even when the amino group is protonated, and when containing a physiologically active substance in the form of an antibacterially active compound or anticancer drug, have the characteristic of exhibiting hardly any toxicity against normal human endothelial cells despite exhibiting the expected physiological activity.

Thus, the silica-containing redox nanosized particles having an antibacterial agent or anticancer drug encapsulated or enveloped therein provided in this manner can be used to prepare a parenteral preparation or an oral preparation in any form that can be provided as a solution or liquid in which the particles are solubilized or uniformly dispersed in an aqueous medium. Since the above-mentioned silica-containing redox nanosized particles can be provided as a solid matter by freeze-drying, the particles can be provided as a tablet, pill, or granules by using a vehicle or diluent routinely used in the relevant technical field of the particles per se. Furthermore, with respect to the present invention, the terms encapsulated and enveloped are used interchangeably.

These nanoparticles can be conveniently provided by the production method of the above-mentioned aspect described in (10). Here, the copolymer of formula (I), tetraalkoxysilane or nanosized silica particles and a physiologically active substance are filled into a dialysis container as a solution in a water-soluble organic solvent such as dimethylformamide (DMF) or tetrahydrofuran (THF). Although the container may be any container, it is acceptable as long as it has a shape that is able to withstand use, such as a dialysis tube having a molecular weight cutoff of 12 kDa to 14 kDa. Dialysis is carried out against water for an amount of time and number of times sufficient for forming the target silica-containing redox nanoparticles. Since specific conditions are subsequently described, a person with ordinary skill in the art can carry out dialysis while making modifications as necessary with reference thereto.

As was previously described, since the above-mentioned method can be applied to poly(quaternary amine) antibacterial agents and hydrophobic anticancer drugs that have completely different chemical properties, any of these are included in the physiologically active substance provided they are poly(quaternary amine) antibacterial agents or hydrophobic anticancer drugs which are themselves known while also being in line with the object of the present invention. A typical example of the above-mentioned antibacterial agent is an antibacterial compound represented by:

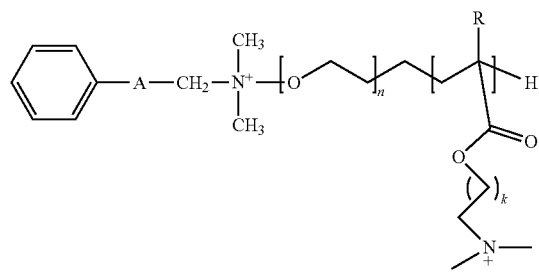

in the formula,

A is represented by —$(CH_2)_j$—, where j is 0 or an integer of 1 to 17;

R is a hydrogen atom or methyl group; and at least one of 1 to 5 hydrogen atoms in phenyl may be replaced with $C_{1-6}$ alkyl, $C_{1-6}$ alkoxy or hydroxy. On the other hand, examples of hydrophobic anticancer drugs include BNS-22 (8-[(3,4-dihydro-2H-quinolin-1-yl)carbonyl]-5,7-dimethoxy-4-propyl-2H-chromen-2-one),
sorafenib, camptothecin, paclitaxel, and anticancer platinum complexes (such as cisplatin, carboplatin, nedaplatin, or oxaliplatin).

In general, the above-mentioned antibacterial agent can be produced in accordance with the reaction scheme indicated below.

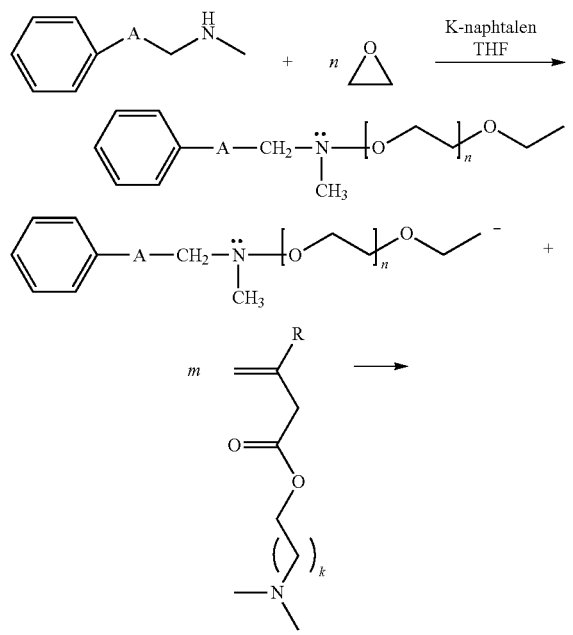

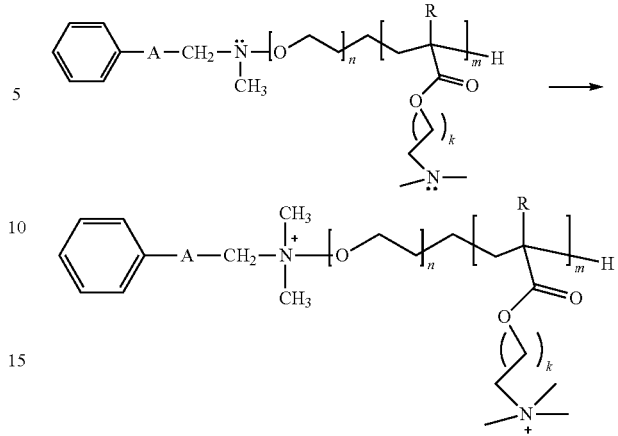

In addition, any hydrophobic anticancer drug can be used provided the drug per se is known and is a compound that has low solubility in water as is observed with BNS-22.

Although silica-containing redox nanoparticles having a physiologically active substance encapsulated therein cannot be specified since the maximum encapsulated amount varies according to the properties and chemical structure of the physiologically active substance, in the case of, for example, the physiologically active substance is BDMA-PEG-b-PTMAEMA, which will be described later, having low toxicity, the weight ratio of the physiologically active substance to the copolymer of formula (I) can be made to be 2:1 to 400:1 and preferably 4:1 to 200:1.

In the relevant technical field, antibacterial peptides are being known to have bactericidal action by selectively destroying the bacterial membrane by electrostatic action due to the amphiphilic and cationic properties thereof. Although the development of resistance has been considered to be a serious problem with conventional antibiotics as exemplified by penicillin since these antibiotics demonstrate antimicrobial action based on inhibition of protein function and the like, since antibacterial peptides are based on physical damage, they are considered to be comparatively unlikely to cause the development of resistance and several research projects are being conducted related thereto. In recent years, development is also proceeding not only on peptides, but also on antibacterial polymers that imitate these peptides. The above-mentioned nanoparticles of the present having an antibacterial agent packaged therein are following this trend. Moreover, since a redox function or silica adsorption function of the cyclic nitroxide radical simultaneously contained within these particles is exhibited, these particles can be preferably used in the prevention and/or treatment of bacterial peritonitis, for example, and particularly intraperitoneal infections in peritoneal dialysis patients. In addition, silica-containing redox nanoparticles having an anticancer drug packaged or enveloped therein are stable under acidic conditions and high ionic strength conditions, and as was previously described, can be administered parenterally or orally, they can be preferably used in the prevention and/or treatment of cancer of the digestive system.

The dose of the silica-containing redox nanoparticles having a physiologically active substance packaged therein in the case of using to treat a disease as described above is not limited since the optimum value varies according to such factors as the type and degree of the disease, and can be determined by a specialist based on data and the like obtained by conducting small-scale animal studies, for example.

EXAMPLES

Although the following provides a more detailed explanation of the present invention by referring to specific examples thereof, the present invention is not intended to be limited thereto.

Production Example 1: Synthesis of Poly(ethylene glycol)-block-poly(chloromethylstyrene) (PEG-b-PCMS) Diblock Copolymer PEG-b-PCMS was synthesized in accordance with the Synthesis Scheme 1 indicated below.

Methoxypolyethylene glycol having a hydroxy group on ends thereof (PEG-OH, Mn: 5000, 3 mmol, 15 g) was dehydrated by vacuum drawing for 12 hours at 110° C. Subsequently, the atmosphere was replaced with nitrogen followed by the addition of 60 mL of tetrahydrofuran (THF). Next, n-butyl lithium (BuLi, 0.384 g, 6 mmol) was added thereto. Moreover, α,α'-dichloroparaxylene (5.25 g, 30 mmol) was added to synthesize polyethylene glycol-chloroparaxylene (PEG-Cl). Purification treatment was carried out by precipitating against isopropyl alcohol (quantitative yield: 13.77 g, yield percentage: 91.8%). Carbon disulfide (0.974 g, 12.8 mmol) and benzomagnesium bromide (polyethylene glycol having a chain initiator on the end thereof, PEG-CTA) were recovered (quantitative yield: 7.76 g, yield percentage: 97%). PEG-CTA (Mn: 5000, 0.7 mmol, 3.5 g) was then added to the reaction vessel. Next, a procedure including vacuum drawing the inside of the reaction vessel followed by blowing in nitrogen gas was repeated three times to replace the atmosphere within the reaction vessel with nitrogen. Azobisisobutyronitrile (AIBN, 114.9 mg, 0.7 mmol) and chloromethylstyrene (21 mmol, 3 mL) were added to the reaction vessel followed by heating to 60° C. and stirring for 24 hours. After washing the reaction mixture three times using diethyl ether, which is a good solvent with respect to poly(chloroethylsytrene) homopolymer, the reaction mixture was freeze-dried with benzene to obtain a skin-colored powder. As a result, synthesis of polyethylene glycol-polychloromethylstyrene (PEG-b-PCMS) was completed and the quantitative yield was 4.45 g (yield percentage: 72%). The separation spectrum and NMR spectrum as determined by size exclusion chromatography (SEC) are shown in FIG. 1.

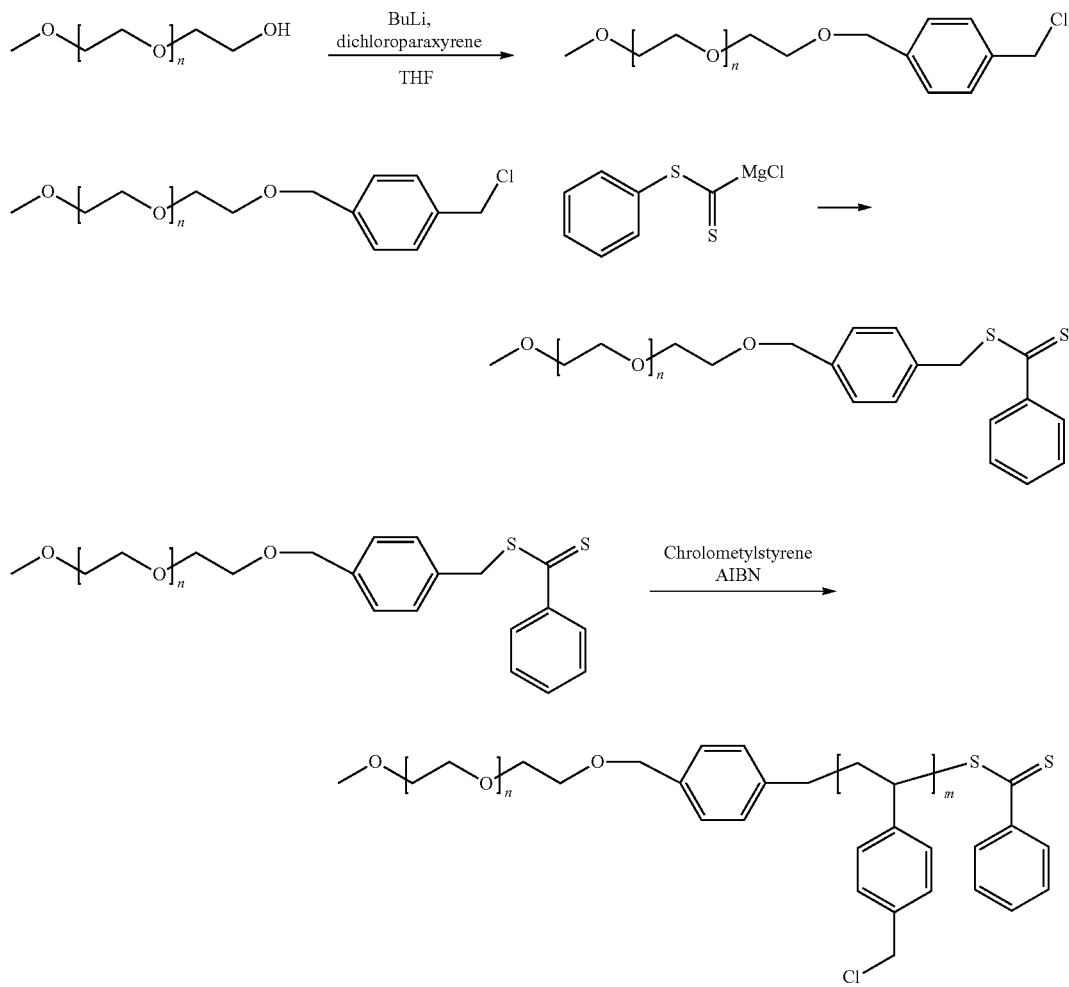

Synthesis Scheme 1

Production Example 2: Synthesis of Diblock Polymer Having Styrene Polymer Randomly Bonded to TEMPO and Silica (PEG-b-PMNT-Si)

PEG-b-PMNTPSi was synthesized in accordance with Scheme 2 indicated below.

Scheme 2

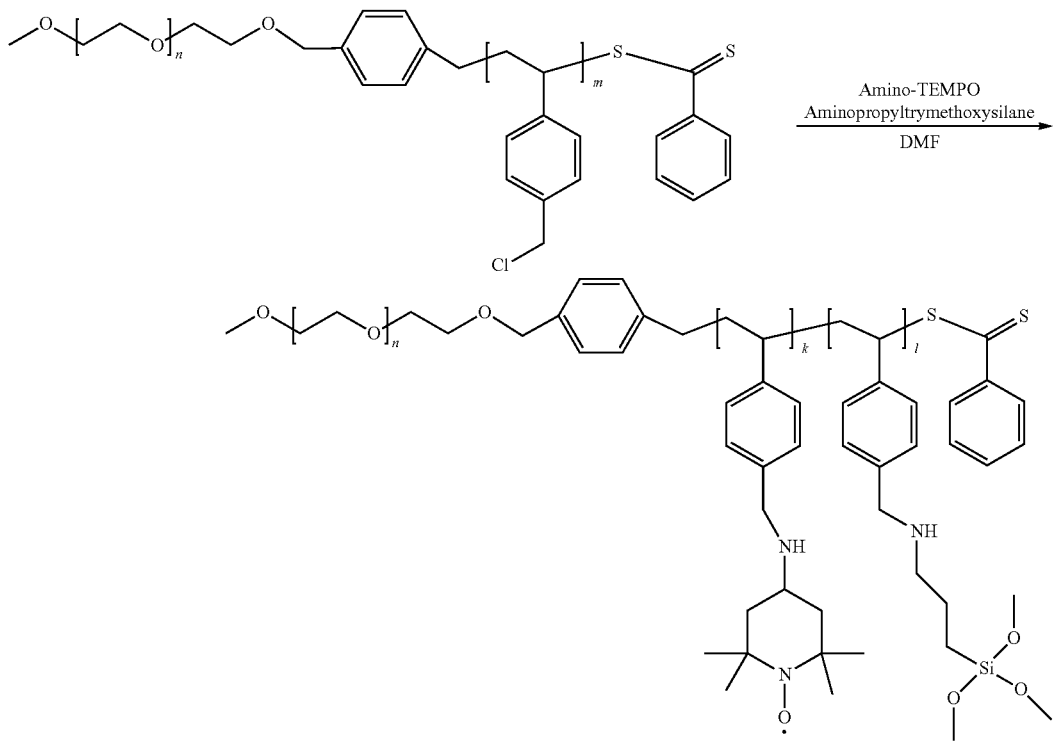

PEG-b-PCMS (Mn: 8878, 1.191 g, 0.14 mmol) was added to a reaction vessel. This was dissolved with 8 mL of N,N-dimethylformamide (DMF). Next, 4-amino-2,2,6,6-tetramethylpiperidine 1-oxyl (Amino-TEMPO, 2.5 g, 14.6 mmol) was dissolved in 4 mL of DMF and added to the reaction vessel followed by the addition of aminopropyltrimethoxysilane (APTMS, 0.261 g, 1.46 mmol) and stirring at room temperature for 24 hours.

Production Example 3: Synthesis of Benzylmethyl-amino-PEG-b-polymethacrylate [2-(N,N-dimethyl-aminoethyl] (BMA-PEG-b-PDMAEMA)

BMA-PEG-b-PDMAEMA was synthesized in accordance with Scheme 3 indicated below.

Scheme 3

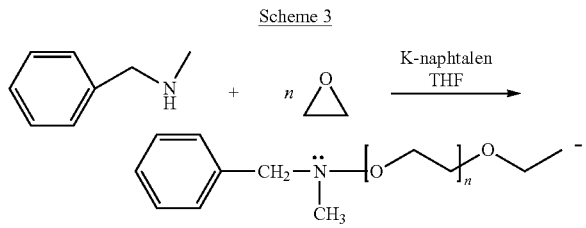

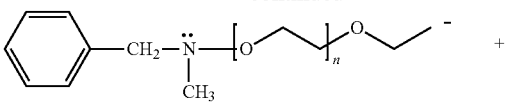

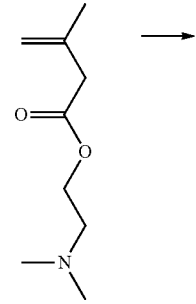

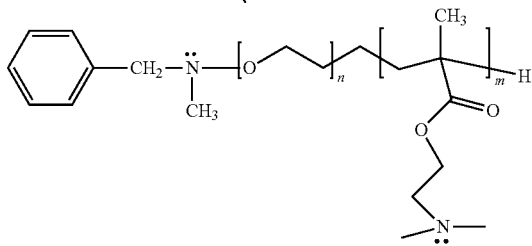

150 mL of THF, 0.3 g of 1-phenylethylenediamine and potassium naphthalene (3 mL, 0.9 M) were added to a reaction vessel followed by the further addition of 12 g of ethylene oxide and stirring at room temperature for 24 hours to synthesize polyethylene glycol having benzylmethylamine on the end thereof by anionic polymerization. Subsequently, dimethylaminoethyl methacrylate (12 g) were added followed by stirring at room temperature for 24 hours to synthesize benzylmethylamine polyethylene glycol-b-polymethacrylate [2-(N,N-dimethyl)aminoethyl]. Purification was carried out by precipitating with diethyl ether. The separation spectrum and NMR spectrum as determined using a size exclusion chromatography (SEC) column are shown in FIG. 2.

Production Example 4: Synthesis of Benzyldimethylamine-PEG-b-polymethacrylate [2-(N,N,N-trimethyl)aminoethyl] (BDMA-PEG-b-PTMAEMA)

BDMA-PEG-b-PTMAEMA was synthesized in accordance with Scheme 4 indicated below.

Scheme 4

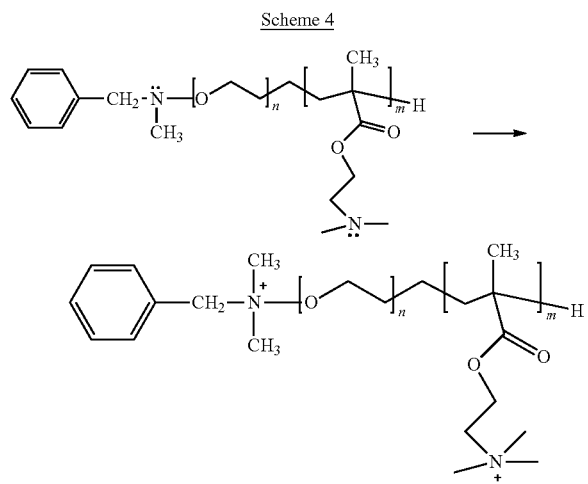

BMA-PEG-b-PDMAEMA (6 g) was placed in a reactor followed by dissolving in THF (30 mL) and adding methyl iodide (5 g). The reaction mixture was stirred for 24 hours at room temperature. Purification was carried out by precipitating with isopropyl alcohol to obtain a yellow powder. The NMR spectrum is shown in FIG. 3.

Production Example 5: Design of Silica-containing Redox Nanoparticles (siRNP) Using TEOS 2.8 g of the PEG-b-PMNT-Si reaction mixture obtained in Production Example 2 (containing 480 mg of active ingredient), 333 mg of tetraethoxysilane (TEOS) and 48 mL of DMF were mixed, placed in a dialysis tube (molecular weight cutoff: 12 kDa to 14 kDa) and dialyzed against 2 L of water. The water was replaced five times every 12 hours. The resulting solution was used to prepare high ionic strength water (NaCl=0.3 M) and acidic water (pH=2.0), and the results of measuring light scattering and zeta potential 24 hours later are shown in FIG. 4.

It was found from FIG. 4 that the average particle diameter and surface zeta potential under high ionic strength were 38.3 nm and −0.6 mV, respectively, while the average particle diameter and surface zeta potential under the condition of pH=2.0 were found to be 39.8 nm and 14.6 mV, respectively, and the particles were confirmed to be stable without exhibiting aggregation under high ionic strength and without demonstrating collapse of the particles under the acidic condition even when the amino group was protonated.

There were no changes in ESR intensity before and after preparation and stable silica-containing redox nanoparticles were able to be produced without requiring heat treatment that presented a problem in the past.

Next, dialysis was carried out in the same manner to obtain three types of dialysates of nanoparticles consisting of (I) PEG-b-PMNT micelles, (II) PEG-b-PMNT-Si nanoparticles, and (III) 60% (SiO$_2$ weight/polymer weight) mixture of PEG-b-PMNTSi and TEOS. As a result, particles that had the particle diameters shown in the graph on the right side of FIG. 5 as determined by analyses using dynamic light scattering (DLS) were obtained, and as a result of analyzing the Si content thereof by inductively coupled plasma mass spectrometry (ICP-MASS), particles that had the silica contents shown in FIG. 5 corresponding to the amount of TEOS introduced were able to be obtained.

Production Example 6: Design of siRNP Using Silica Sol 2.8 g of the PEG-b-PMNTPSi reaction mixture obtained in Production Example 2 (containing 480 mg of active ingredient), 320 mg of methanol silica sol (Nissan Chemical Corporation, 10 to 15 nm) and 48 mL of DMF were mixed, placed in a dialysis tube (molecular weight cutoff: 1 kDa to 14 kDa) and dialyzed against 2 L of water. The water was replaced five times every 12 hours. The resulting solution was used to prepare high ionic strength water (NaCl=0.3 M) and acidic water (pH=2.0) and the results of measuring light scattering and zeta potential 24 hours later are summarized in FIG. 6. It was found from FIG. 6 that the average particle diameter and surface zeta potential under high ionic strength were 42.0 nm and −0.17 mV, respectively, while the average particle diameter and surface zeta potential at pH=2.0 were found to be 36.2 nm and 15.2 mV, respectively, and the particles were confirmed to be stable without exhibiting aggregation under high ionic strength and without demonstrating collapse of the particles under an acidic condition even when the amino group was protonated.

There were no changes in ESR intensity before and after preparation and stable silica-containing redox nanoparticles were able to be produced without requiring heat treatment that presented a problem in the past.

Production Example 7

2.8 g of the PEG-b-PMNT-Si reaction mixture obtained in Production Example 2 (containing 480 mg of active ingredient) were mixed with 48 mL of DMF, placed in a dialysis tube (molecular weight cutoff: 12 kDa to 14 kDa) and dialyzed against water. The water was replaced five times every 12 hours. The resulting solution was used to prepare high ionic strength water (NaCl=0.3 M) and acidic water (pH=2.0) and the results of measuring light scattering and zeta potential 24 hours later are summarized in FIG. 7. It was found from FIG. 7 that the average particle diameter and surface zeta potential under high ionic strength were 73.1 nm and 1.26 mV, respectively, while the average particle diameter and surface zeta potential under the acidic condition were found to be 45.9 nm and 20.2 mV, respectively, and the particles were confirmed to be stable without exhibiting aggregation under high ionic strength and without demonstrating collapse of the particles under an acidic condition even when the amino group was protonated.

There were no changes in ESR intensity before and after preparation and stable silica-containing redox nanoparticles were able to be produced without requiring heat treatment that presented a problem in the past.

Production Example 8: Design of Silica-containing Cationic Redox Nanoparticles (Cation siRNP)

PEG-b-PMNT-Si (130.9 mg) dissolved in DMF, BDMA-PEG-b-PTMAEMA (104 mg) dissolved in THF, and TEOS were mixed followed by the addition of aqueous ammonia (0.7 mL), stirring, placing in a dialysis membrane, and dialyzing against water. The mixed amounts were in accordance with Table 1. Two liters of water were replaced three times after 12 hours, 6 hours and 3 hours followed by measurement of average particle diameter by dynamic light scattering. As a result, nanoparticles of 30 to 60 nm were confirmed to have been formed. Particle diameter was confirmed to change dependent on the mixed amount of silica. These results are shown in Table 2.

TABLE 1

|  | TEOS | Zeta potential (mV) | Average particle diameter (nm) |
| --- | --- | --- | --- |
| Cation siRNPT | 0 μL | 3.57 | 35.81 |
| TEOS containing 20% Cation siRNP | 89.96 μL | 4.91 | 47.65 |
| TEOS containing 60% Cation siRNP | 269.88 μL | 4.48 | 60.2 |

TABLE 2

|  | PEG-b-PMNT-Si (mg) | BDMA-PEG-b-PTMAEMA (mg) | Molar ratio |
| --- | --- | --- | --- |
| Cation siRNPT (4:1) | 131 | 52 | 4:1 |
| Cation siRNPT (20:1) | 131 | 8 | 20:1 |
| Cation siRNPT (100:1) | 131 | 5.2 | 100:1 |
| Cation siRNPT (200:1) | 131 | 0.8 | 200:1 |

A plurality of mixtures of having different ratios of the introduced amounts of PEG-b-PMNT-Si and BDMA-PEG-b-PTMAEMA was prepared according to the same method. The ratios were in accordance with Table 2. Zeta potential was observed to change due to a reduction BDMA-PEG-b-PTMAEMA and there were no effects on particle diameter. The results are summarized in Table 3 indicated below.

TABLE 3

|  | Zeta potential (mV) | Average particle diameter (nm) |
| --- | --- | --- |
| Cation siRNPT (4:1) | 131 | 34.65 |
| Cation siRNPT (20:1) | 131 | 32.41 |
| Cation siRNPT (100:1) | 131 | 31.67 |
| Cation siRNPT (200:1) | 131 | 35.36 |

Test 1: Evaluation of Antibacterial Effect of Silica-Containing Cationic Redox Nanoparticles (Cation siRNP) on *Staphylococcus aureus* (JCM 2151)

Cation siRNP prepared in the manner described above was mixed with Mueller-Hinton Broth, serially diluted and dispensing in 50 μL aliquots followed by the addition thereto of 50μ aliquots of 1×10$^6$ CFU/mL of *Staphylococcus aureus* (JCM 2151, available from the Japan Collection of Microorganisms, BioResource Research Center, RIKEN) and mixing in a 96-well plate. The antibacterial activity thereof was confirmed by culturing for 20 hours and calculating the minimum inhibitory concentration (MIC). Concentration was determined by converting for the PEG-b-PMNT-Si polymer. The results are shown in Table 4.

TABLE 4

| Minimum inhibitory concentration (MIC) | |
| --- | --- |
|  | mg/mL |
| Cation siRNPT | 0.031 |
| TEOS containing 20% Cation siRNP | 0.042 |
| TEOS containing 60% Cation siRNP | 0.042 |
| Cation siRNPT (4:1) | 0.031 |
| Cation siRNPT (20:1) | 0.125 |
| Cation siRNPT (100:1) | 0.333 |
| Cation siRNPT (200:1) | 2.000 |

Test 2: Evaluation for Tobxicity of Silica-Containing Redox Nanoparticles on Bovine Aortic Endothelial Cells Toxicity at the determined MIC concentration was evaluated using normal tissue cells in the form of bovine aortic endothelial cells (BAEC).

The cells were cultured using culture broth containing fetal bovine serum (FBS) in Dulbecco's Modified Eagle Medium (DMEM) at a concentration of 10%. After seeding 96-well plates with 5000 cells each, each of the nanoparticles were administered to the cells at the MIC concentration 24 hours later. Subsequently, absorbance at 450 nm was measured 24 hours later using the WST-8 kit reagent 2 hours after dropping in the reagent, and after subtracting the measured value of a blank, the survival ratios were calculated by dividing by the value of the control. The results are shown in FIG. 8. It was found from FIG. 8 that toxicity and antibacterial activity can be adjusted according to the introduction ratios of PEG-b-PMNT-Si and BDMA-PEG-b-PTMAEMA. As a result, silica-containing redox nanoparticles were created by determining the optimum ratio having antibacterial activity with low toxicity. In addition, toxicity tended not to be demonstrated as a result of evaluating the toxicity of the nanoparticles at concentrations two and three times higher than the MIC concentration. The results are shown in FIG. 9.

Production Example 9: Design of Redox Nanoparticles Containing BNS-22 and Silica (BNS-22 siRNP)

(1) Nanoparticle Production Example

In order to encapsulate BNS-22 in the nanoparticles, 10 mg (20% by weight based on polymer weight) or 20 mg (40% by weight based on polymer weight) of BNS-22 were added to a solution of PEG-b-PMNT-Si (50 mg) dissolved in DMF followed by stirring for 24 hours. Next, dialysis was carried out for 24 hours against water. The resulting nanoparticles were designated as siRNP.

In addition, 90 μL (83.97 mg) of TEOS and 10 mg or 20 mg each of BNS-22 were added to a solution of PEG-b-PMNT-Si (50 mg) dissolved in DMF followed by stirring for 24 hours. Next, dialysis was carried out for 24 hours against water. The resulting nanoparticles had an average particle diameter of about 80 nm as determined by DLS. These particles were hereinafter designated as siRNP+TEOS. Following dialysis, encapsulation of BNS-22 was evaluated by measuring absorbance by utilizing the properties of BNS-22 having a maximum absorption wavelength of 315 nm. The results are shown in FIG. 10.

It was found from FIG. 10 that the encapsulation efficiency of BNS-22 increases significantly to 10% to 12% for siRNP, whereas 7% to 8% for RNP(N) (see, for example, Patent Document 1), which are conventional nanoparticles. As a result of having TEOS also co-present in the nanoparticle formation system, encapsulation efficiency further increased to 17% to 18% in the resulting siRNP+TEOS particles. Although the liquid became cloudy when the drug was attempted to be encapsulated in RNP(N) in a large amount, since the liquid remained clear during the use of siRNP, siRNP was determined to have a high drug encapsulation efficiency in comparison with RNP(N).

(2) Stability Test of Nanoparticles Under Acidic Conditions

Each of the nanoparticle-containing solutions obtained in accordance with (1) was used to prepare acidic water (pH=2.5 in stomach) and the status of the particles was evaluated over time by measurement of DLS. The results are shown in FIG. 11.

It was determined from FIG. 11 that siRNP and siRNP+TEOS are more stable under a low-acidic condition in comparison with RNP-N able to be prepared according to conventional methods.

(3) Test of Release of Drug from Nanoparticles

Aqueous solutions (pH=2.5 and pH=7.5) containing 0.5% by weight of siRNP+TEOS were allowed to stand undisturbed at room temperature followed by measurement of the amount of free drug over time. The results are shown in FIG. 12.

It was found from FIG. 12 that siRNP+TEOS resulted in the gradual release of drug from the nanoparticles at both pH=2.5 and pH=7.5.

(4) Pharmacokinetic Study of Nanoparticles

A 0.75% by weight aqueous solution of BNS-22-containing siRNP obtained in (1) above (BNS-22@siRNP+TEOS, that having the highest drug inclusion rate among the above) was orally ingested by 8-week-old mice (ICR mice). Blood samples were collected from the animals over time followed by detection of drug plasma concentration. A 0.5% by weight carboxymethyl cellulose solution of the drug (BNS-22 (CMC 0.5%)) was similarly orally ingested by the animals as a control. The results are shown in FIG. 13.

The results are shown together with the results of AUC analysis in FIG. 14.

Based on the drawing, highly-concentrated BNS-22 was detected in the blood following oral administration of BNS-22@siRNP. As a result of analyzing the concentration of drug in the blood by area under the curve (AUC) analysis in order to more thoroughly evaluate bioavailability, the AUC of BNS-22@siRNP was confirmed to increase considerably in comparison with BNS-22. These results suggest that the bioavailability of BNS-22 is improved by siRNP.

Test 3: Evaluation of Antibacterial Activity of Silica-Containing Cationic Redox Nanoparticles (Cation siRNP) in Mouse Abdominal Cavity This test was carried out to evaluate antibacterial activity of prepared cationic silica-containing redox nanoparticles (Cationic siRNP) using mice assuming the situation in which bacteria has entered the abdominal cavity of peritoneal dialysis patients.

Bacteria in the form of *Staphylococcus aureus* (strain JCM 2151) were injected into the abdominal cavity of ICR mice at $1 \times 10^8$ CFU. Subsequently, Cationic siRNP was administered at 250 mg/Kg (mouse body weight), 125 mg/Kg and 61.25 mg/Kg as the concentration of PEG-b-PMNT-Si. The abdominal cavity was then washed with physiological saline 12 hours later and the wash was cultured in TSB-agar medium following by a comparison of the number of colonies.

Protocol:

*S. aureus* (JCM 2151) was injected into the abdominal cavity of 8-week-old ICR(Cr) mice at $1 \times 10^8$ CFU (500 µL). The test was carried out in groups of six mice each. An overview of the protocol is shown in FIG. 15 and the test results are shown in FIG. 16.

It can be found from FIG. 16 that silica-containing cationic redox nanoparticles exhibited remarkable antibacterial activity at a concentration of 250 mg/Kg and that trend was also observed even at lower concentrations.

Test 4: Evaluation of Toxicity of Cationic Silica-Containing Redox Nanoparticles during Intraperitoneal Administration to Mice Toxicity during administration of Cationic siRNP into the abdominal cavity was evaluated by measuring blood markers and blood electrolyte concentrations. Namely, Cationic siRNP was administered into the abdominal cavity of ICR mice (age: 9 weeks, ICR(Cr), 5 mice per group) at 250 mg/Kg (mouse body weight, group G.2) and 62.5 mg/Kg (group G.3) as the concentration of PEG-b-PMNT-Si. Furthermore, an untreated control group was designated as group G.1. Blood was collected from the heart 24 hours later, and after removing blood cells by centrifugal separation, serum proteins were measured using the Fuji Dri-Chem 7000V dry chemistry analyzer (Fujifilm Corporation). The results are shown in FIGS. 17, 18 and 19. On the basis of these graphs, remarkable systemic toxicity was considered to not be observed for Cation siRNP in the abdominal cavity of mice at concentrations that demonstrate antibacterial activity.

Production Example 10: Design of Redox Nanoparticles Containing Sorafenib and Silica (Sorafenib siRNP)

(1) Introduction

The oral kinase inhibitor, sorafenib, has been used for progressive hepatic cancer and renal cancer. It has recently been known to exhibit antifibrotic activity in animal models of hepatic fibrosis. However, the use thereof in the clinical setting has been limited due to its extremely low solubility in water and low bioavailability.

In this production example and tests, an attempt was made to encapsulate and solubilize sorafenib in the previously described siRNP.

(2) Nanoparticle Production Example and Determination of Properties Thereof 10 mg of sorafenib were added to vials containing 100 mg of PEG-siPMNT in 1 mL of DMF containing various TEOS (up to 75% of $SiO_2$). Next, 20 µL of $NH_3$ were added followed by stirring the mixture for 2 hours at room temperature. The mixture was transferred to a dialysis membrane tube (MWCO: 3.5 kDa) and dialyzed against distilled water. The dialysate was replaced several times during dialysis.

Drug encapsulation efficiency (EE) and drug loading capacity (LC) were determined by HPLC using UV detection at 254 nm. The results are shown in Table 5 below.

TABLE 5

Drug encapsulation efficiency (EE) and drug loading capacity (LC)

|  | EE (%) | LC (%) |
|---|---|---|
| sorafenib@siRNP 0% | 88.94 | 8.89 |
| sorafenib@siRNP 10% | 89.27 | 8.93 |
| sorafenib@siRNP 25% | 92.27 | 9.29 |
| sorafenib@siRNP 50% | 96.22 | 9.63 |
| sorafenib@siRNP 75% | 100.04 | 10.00 |

Note:
Drug encapsulation efficiency (EE) (%) = Weight of drug in nanoparticles/weight of drug used
Drug loading capacity (%) = Weight of drug in nanoparticles/weight of nanoparticles used (3) Evaluation of Antifibrotic Activity Antifibrotic activity was evaluated for sorafenib and sorafenib@siRNP using an immortalized cell line TWNT-1 (CVCL J364) of hepatic stella cells that play an important role in the pathogenesis of hepatic fibrosis. Various concentrations of sorafenib and sorafenib@siRNP were added to a 96-well plate (5000 cells/well) using a cell proliferation assay kit (MMT kit) followed by incubating for 2 days. In the case of this assay kit, it is necessary to note that, although the sorafenib@siRNP can be dissolved in phosphate-buffered saline (PBS), free sorafenib is required to be dissolved in dimethylsulfoxide (DMSO). The evaluation results are shown in FIG. 20. The graph on the left indicates the evaluation results for TWNT-1 while the graph on the right indicates the evaluation results for normal endothelial cells (BAEC).

It can be found from the graph on the left that sorafenib@siRNP maintains the activity of sorafenib that inhibits the proliferation of TWNT-1, thereby exhibiting antifibrotic effects. On the other hand, based on the graph on the right, sorafenib@siRNP exhibits low toxicity against normal endothelial cells that is significantly superior in comparison with free sorafenib. This result indicates that, simultaneous to the use of siRNP making it possible to solubilize a hydrophobic drug in the manner of sorafenib, it is also able to suppress detrimental effects on normal cells while retaining the biological activity of the drug.

The invention claimed is:

1. A copolymer represented by formula (I):

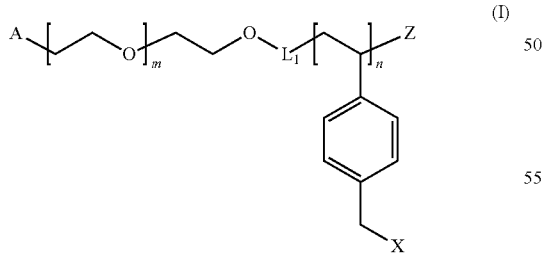

wherein:

A represents a non-substituted or substituted $C_1$-$C_{12}$ alkoxy group, wherein in the substituted $C_1$-$C_{12}$ alkoxy group, the substituent is selected from the group consisting of a formyl group and a R'R"CH— group, wherein R' and R" independently represent $C_1$-$C_4$ alkoxy or R' and R" together combine to form —OCH$_2$CH$_2$O—, —O(CH$_2$)$_3$O— or —O(CH$_2$)$_4$O—;

$L_1$ is selected from the group consisting of:

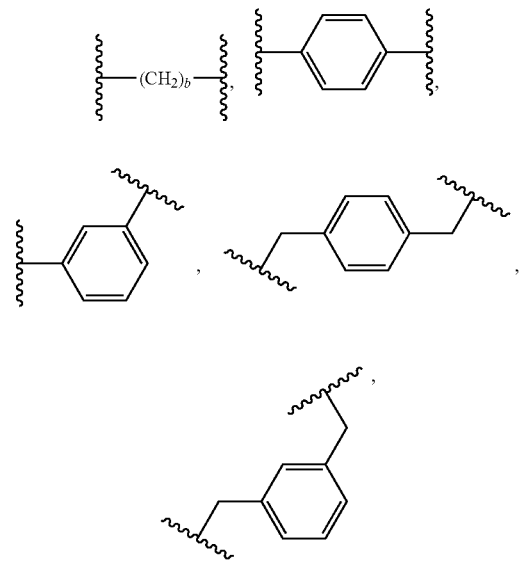

a single bond, —(CH$_2$)$_b$S—, —CO(CH$_2$)$_b$S—, —(CH$_2$)$_b$NH—, —(CH$_2$)$_b$CO—, —CO—, —OCOO—, and —CONH—;

X is selected from the group consisting of:

(a) a group represented by $L_2$-$R_1$, wherein $L_2$ represents —(CH$_2$)$_a$—NH—(CH$_2$)$_a$— or —(CH$_2$)$_a$—O—(CH$_2$)$_a$— and $R_1$ is any of the following formulas:

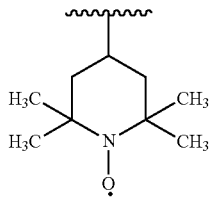 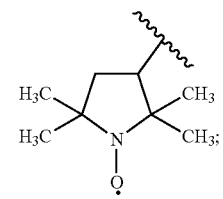

(b) a group represented by $L_3$-$R_2$, wherein $L_3$ represents —(CH$_2$)$_a$—NH—(CH$_2$)$_a$— or —(CH$_2$)$_a$—O—(CH$_2$)$_a$-, $R_2$ is —(CH$_2$)$_k$—Si(O-Alk)$_3$, and each Alk is a $C_{1-4}$ alkyl that may be the same as or different from another Alk; and (c) a group represented by $R_3$, wherein $R_3$ is chloro, bromo, or hydroxy;

wherein units present in a polymer main chain having (a), (b) and (c) are randomly present, units having (a) are within a range of 3 to 80, units having (b) are within a range of 3 to 80, and units having (c) are either not present or within a range of 1 to 20, provided that the total number of these units is n;

Z is H, SH, or S(C=S)—Ph, wherein Ph represents phenyl optionally substituted with one or two groups of methyl or methoxy;

each a independently represents 0 or an integer of 1 to 5;

b represents an integer of 1 to 5;

k represents an integer of 1 to 18;

m represents an integer of 2 to 10,000;
n represents an integer of 6 to 100;
wherein the repeating unit

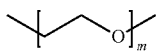

is a hydrophilic segment, and the repeating unit

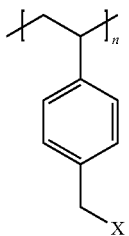

is a hydrophobic segment; and
wherein copolymers represented by the formula (I) form nanosized particles under acidic conditions having a pH of 2 in an aqueous solution or an aqueous homogeneous dispersion due to the presence of $-(CH_2)_k-Si(O-Alk)_3$ in the $L_3$-$R_2$ group in the copolymers.

2. The copolymer according to claim 1, wherein $L_1$ represents paraxylylene, metaxylylene, or $-CH_2CH_2S-$, $L_2$ represents $-NH-$ or $-O-$, and each of the Alk is the same as another.

3. A pharmaceutical composition comprising the copolymer represented by formula (I) according to claim 1 and a poly(quaternary amine) antibacterially active substance.

4. The composition according to claim 3, which forms nanosized micellar particles in an aqueous medium.

5. A pharmaceutical composition comprising the copolymer represented by formula (I) according to claim 1 and a hydrophobic anticancer drug.

6. The composition according to claim 5, wherein the hydrophobic anticancer drug is selected from the group consisting of 8-[(3,4-dihydro-2H-quinolin-1-yl)carbonyl]-5,7-dimethoxy-4-propyl-2H-chromen-2-one, sorafenib, camptothecin, paclitaxel, and an anticancer platinum complex.

7. The composition according to claim 5, which forms nanosized micellar particles in an aqueous medium.

8. The composition according to claim 6, which forms nanosized micellar particles in an aqueous medium.

9. Pharmaceutical silica-containing redox nanoparticles comprising a biologically active substance encapsulated or filled therein, wherein the copolymer of the formula (I) of claim 1 is immobilized on nanosized silica particles of the pharmaceutical silica-containing nanoparticles via $-(CH_2)_k-Si(O-Alk)_3$ of the $L_3$-$R_2$ group in the copolymer, and wherein a physiologically active substance is bound to or adsorbed on the nanosized silica particles.

10. A method of producing silica-containing redox nanoparticles comprising a physiologically active substance encapsulated or filled therein, the method comprising the steps of:
preparing in a dialysis container a water-soluble mixed solution comprising (1) the copolymer according to claim 1, (2) (i) a tetraalkoxysilane represented by $Si(O-Alk)_4$, wherein each Alk is the same or different $C_{1-4}$ alkyl group or (ii) nano-sized silica particles, and (3) a poly(quaternary amine) antibacterial compound or a hydrophobic anticancer drug as a biologically active substance; and
dialyzing the water-soluble mixed solution against water at a temperature of 10° C. to 30° C.

* * * * *